(12) United States Patent
Colman et al.

(10) Patent No.: US 10,420,925 B2
(45) Date of Patent: Sep. 24, 2019

(54) ADAPTER

(71) Applicant: ORIDION MEDICAL 1987 LTD., Jerusalem (IL)

(72) Inventors: Joshua Lewis Colman, Jerusalem (IL); Avi Finkelstein, Zur Igal (IL); Philip Roy, Lafayette, CO (US); Roni Peer, Yehud (IL); Noam Erlich, Kibbutz Naan (IL); Yigal Krayz, Ashdod (IL); Refael Koby, Kochav Yair (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 687 days.

(21) Appl. No.: 14/995,338

(22) Filed: Jan. 14, 2016

(65) Prior Publication Data

US 2016/0206845 A1    Jul. 21, 2016

Related U.S. Application Data

(60) Provisional application No. 62/105,236, filed on Jan. 20, 2015.

(51) Int. Cl.
*A61M 39/10*    (2006.01)
*A61M 16/08*    (2006.01)

(52) U.S. Cl.
CPC ...... *A61M 39/1011* (2013.01); *A61M 16/085* (2014.02); *A61M 16/0816* (2013.01); *A61M 2039/1077* (2013.01); *A61M 2205/273* (2013.01); *F16L 2201/44* (2013.01)

(58) Field of Classification Search
CPC ............ A61M 16/0816; A61M 16/085; A61M 39/1011; A61M 2039/1077; A61M 2205/273; F16L 2201/44
USPC ...................................... 285/81, 123.15, 330
See application file for complete search history.

(56) References Cited

U.S. PATENT DOCUMENTS

| | | | |
|---|---|---|---|
| 2003/0098430 A1* | 5/2003 | Leinsing | |
| 2004/0060443 A1 | 4/2004 | Richardson | |
| 2012/0123381 A1* | 5/2012 | Kraus | ................ A61M 39/1011 |
| 2014/0152000 A1* | 6/2014 | Chen | ......................... 285/330 X |
| 2015/0247597 A1* | 9/2015 | Okiyama | ........... A61M 39/1011 |
| 2015/0265499 A1* | 9/2015 | Takeuchi | ........... A61M 39/1011 |

FOREIGN PATENT DOCUMENTS

| | | |
|---|---|---|
| JP | 2012/034738 | 2/2012 |
| WO | 2008/014412 | 1/2008 |
| WO | 2013/088439 | 6/2013 |

* cited by examiner

*Primary Examiner* — Greg Binda
*Assistant Examiner* — Zachary T Dragicevich
(74) *Attorney, Agent, or Firm* — Cantor Colburn LLP

(57) ABSTRACT

An adapter configured to allow interconnection of a device input connector (DIC) having a first connector configuration and an consumable end connector (CEC) having a second connector configuration, the adapter including a first end having a first connector mateable with the DIC, a second end configured to receive at least part of the CEC, a locking mechanism configured to lock the CEC to the adapter, and a release mechanism configured to release the CEC from the adapter.

11 Claims, 9 Drawing Sheets

ADAPTER

TECHNICAL FIELD

The present disclosure generally relates to the field of adapters and connectors for interconnection of a consumable to a medical device.

BACKGROUND

Luer Taper is a standardized system of small-scale fluid fittings used for making leak-free connections between a female-taper fitting and its mating male part on medical and laboratory instrument. Key features of Luer connectors are defined in the ISO 594 standards.

The standard Luers are currently being used universally in most medical device categories and applications. However, with the proliferation of medical devices fitted with Luer connectors, and the reports of patient death or injury arising from misconnections, a new ISO standard, 80369-1 requiring different connectors for different categories of medical devices, has been developed.

SUMMARY

Aspects of the disclosure, in some embodiments thereof, relate to adaptable consumables having an alterable connector configuration configured to enable connections to sockets of the old standard (ISO 594) as well as to sockets of the new standard (ISO 80369).

Such adapters may be of particular benefit for connectors used in the field of breath monitoring, in which the transition period from the old to the new standard is prolonged. This is due to the fact that the connectors are found on medical devices and systems that have an average shelf life of several years and, as such, present a major barrier to the changeover since the socket of devices using the old ISO 594 standard will continue to exist and be used for many years after the new standard has been launched. Returning the medical devices to the manufacturer in order to change the device connector is both expensive, time consuming and in some cases even infeasible due to the anticipated new, larger, required dimensions of the connector.

One type of adapters could be adapters configured to interconnect ISO 594 Luer device connectors (also referred to herein as sockets) with connectors conforming with the new ISO 80369 standard. The adapter may thus have a male luer of the ISO 594 connector at one end thereof and a male ISO 80369 connector on its opposing end. This would enable connection between breath sampling devices having a female luer of the ISO 594 configuration with a consumable used for sampling the patient's breath, ending with a female ISO 80369 connector.

However, such adapters would, basically, negate the entire reason for which the new standard has been developed, i.e. to reduce the risk of misconnections between different types of medical equipment. However, if an adapter is not developed, the result may be even more severe; the hospital (or other end user) would need to stock sampling consumables with both configurations of connectors in order to accommodate both the devices having sockets according to the old standard and devices that have been reconfigured to address the new standard. It is easy to envisage the imminent havoc in an emergency situation when a user tries to connect between a consumable that does not match the device intended for its use.

Advantageously, the adapters disclosed herein are configured to reduce the risk of misconnections while addressing the medical needs during the anticipated, inevitable long transition phase.

The adapter disclosed herein is configured to be reversibly locked to a connector of a consumable, thereby generating a consumable having a double configuration connector with an advantageous inherent ability to alter its connector configuration (ISO 594 or ISO 80369) by performing a minimal and simple manual action, which does not require an expert or a technician. For example, during the first few years of the transfer period, the consumable may have a double configuration connector ready for connection to a medical device having an ISO 594 socket (the majority of devices in field), and which upon exerting the simple manual action exposes a new ISO 80369 connector, enabling it to connect to medical devices which have already had their connector bases exchanged. When the number of devices with the new ISO 80369 socket becomes more abundant, the consumable may have a double configuration connector ready for connection with a medical device having an ISO 80369 socket, and which, upon exerting the simple manual action, exposes the old ISO 594 connector. Finally, when most devices have the new ISO 80369 socket, consumables having a single configuration connector of the new ISO 80369 standard only may be utilized.

Advantageously, the double configuration connector may include elements or features which enable a simple identification and/or differentiating between the configuration used for medical devices having a socket according to the old standard and the configuration used for devices that have incorporated the new ISO 80369 sockets.

Importantly, connecting the double configuration connector while utilizing the ISO 594 connector configuration (for connection to a medical device with an ISO 594 socket), does not cause the new ISO 80369 configuration connector to be exposed (i.e. the action of screwing in the ISO 594 connector from the device does not cause the minimal manual action required for changing the connector configuration). Similarly, disconnecting the double configuration connector using the ISO 594 connector configuration from the medical device, does not cause the new ISO 80369 configuration connector to be exposed and thus the ISO 594 connector section to remain connected to the medical device (i.e. the action of unscrewing the ISO 594 connector from the device does not cause the minimal manual action used for changing the connector configuration and/or for separation of the adapter from the connector). This is of outmost importance since if disconnection of the double configuration connector would leave the adapter connected to the medical device, it would prevent connection of a new double configuration connector ready for connection to an ISO 594 socket. Furthermore, the double configuration connector may include means configured to activate the medical device to which it is connected, leaving the adapter connected to the medical device, would thus cause continuous operation of the medical device even when no consumable or patient are connected, and would, as a consequence thereof, result in unnecessary and even detrimental operation of the device, reducing the lifetime thereof.

Advantageously, the double configuration connector disclosed herein is configured to ensure that once the manual action required for exposing the ISO 80369 connector configuration has been performed, and the ISO 594 connector part (the adapter) has been separated therefrom, reconnection of an ISO 80369 connector to the adapter is impossible. This is of outmost importance in that reuse of the adapter or parts thereof would enable to build up a collection of adapters facilitating mating between any ISO 594 connector with a connector of the new ISO 80369 standard, hence rendering the new standard useless.

Similarly, when most devices have the new ISO 80369 socket, consumables having a single configuration connector may be utilized. Beneficially, the present disclosure provides single configuration ISO 80369 connectors having a minor configuration change rendering them incompatible with the adapter, without hampering their compliance with the requirements of the ISO 80369 standard.

According to some embodiments, there is provided an adapter for use in a respiratory gas sampling and/or delivery tubing system, the adapter configured to allow interconnection of a device input connector (DIC) having a first connector configuration and a tube end connector (CEC) having a second connector configuration.

According to some embodiments, the adapter may include a first end having a first connector mateable with said DIC; a second end configured to receive at least part of the CEC; and a locking/release mechanism configured to lock/release the CEC to/from the adapter.

According to some embodiments, the locking/release mechanism may be configured to prevent connection of the first connector to the DIC from releasing the CEC from the adaptor. Additionally or alternatively, the locking/release mechanism may be configured to prevent disconnection of the first connector from the DIC from releasing the CEC from the adaptor.

According to some embodiments, the adapter may include a secondary cone formed within a void of the adapter, the secondary cone configured to mate with a secondary cone formed within a void of the CEC, thereby forming an airtight passageway throughout the adapter and the CEC.

According to some embodiments, the adapter may be non-reusable after activation of said release mechanism. According to some embodiments, the adaptor may include at least one feature rendering it incompatible with a new CEC.

According to some embodiments, the second end of the adapter may include at least one slot configured to slidingly receive a wing of the CEC.

According to some embodiments, the locking mechanism may include a hook configured to hook onto a thread located on an outer surface of the CEC. According to some embodiments, outward displacement of the hook from the thread may release the CEC from the adapter.

According to some embodiments, the locking mechanism may include at least one latch configured to hook onto the CEC. According to some embodiments, the latch may be configured to hook onto a thread located on an outer wall of the CEC. According to some embodiments, the latch may include a protrusion in an inner wall thereof. According to some embodiments, the protrusion may be configured to be received within a notch formed within the thread. According to some embodiments, lifting of the latch by the thread when the CEC is twisted in a counter-clockwise direction relative to the adapter may release the CEC from the adapter. According to some embodiments, the latch may include an opening configured to receive a bulge located on an outer wall of the CEC. According to some embodiments, lifting the latch frees the bulge from the opening, thereby enabling release of the CEC from the adapter.

According to some embodiments, the adapter may include a thread mechanism allowing the CEC to be screwed into the adapter. According to some embodiments, the locking mechanism may include a locker configured to lock the CEC to the adapter after the CEC has been screwed into the adapter. According to some embodiments, the locker may include a protrusion in an inner wall thereof, the protrusion configured to be received within an opening or an indentation in an outer wall of the adapter, thereby preventing the CEC from being unscrewed from the adapter. According to some embodiments, breaking off the locker enables unscrewing the CEC from the adapter. According to some embodiments, the locker may further include an extension configured to engage with the CEC. According to some embodiments, the extension may be configured to engage with at least one wing of the CEC. According to some embodiments, the extension may include a rail in an inner wall thereof, the rail configured to match with at least one protruding section formed on an outer wall of the CEC. According to some embodiments, the locker may include at least two asymmetrical indentations in an inner wall thereof, the at least two asymmetrical indentations configured to mate with asymmetrical threads positioned on an outer wall of the CEC, thereby preventing the CEC to be unscrewed from the adapter.

According to some embodiments, the adapter may include a feature visibly distinguishing the adapter from the CEC.

According to some embodiments, the adapter may include a tubing interconnecting (and spacing) between the first end and the second end of said adapter. According to some embodiments, the tubing may be configured to allow undisturbed gas flow from the CEC, through the tubing to the DIC. According to some embodiments, the tubing may be a flexible tubing.

According to some embodiments, there is provided a double configuration connector for use in a respiratory gas sampling and/or delivery tubing system, the double configuration connector including an adapter having a first end and a second end. The first end of the adapter includes a first connector having a first connector configuration; a consumable end connector (CEC) having a second connector configuration; the CEC being locked to the second end of the adapter, the double configuration connector thereby being of a first connector configuration exposing the first connector and configured for connection to a first device input connector (DIC) having a connector configuration mateable with the first connector configuration. The double configuration connector further includes a release mechanism configured to release the CEC from the adapter, thereby changing the connector configuration of the double configuration connector into a second connector configuration, the second connector configuration exposing the CEC, and configured for connection to a second DIC having a connector configuration mateable with the second connector configuration.

According to some embodiments, the release mechanism is prevented from being activated by connection and/or disconnection of the first connector to and/or from the first DIC.

According to some embodiments, the double configuration connector may be non-reusable after activation of the release mechanism.

According to some embodiments, the second end of the adapter may include at least one slot, wherein a wing positioned on the CEC is received within the slot.

According to some embodiments, the second end of the adapter may include a hook hooked onto a thread, the thread located on an outer surface of the CEC. According to some embodiments, the release mechanism may include an outward displacement of the hook from the thread, thereby enabling the release of the CEC from the adapter.

According to some embodiments, the adapter may include at least one latch hooked onto the CEC. According to some embodiments, the latch may be hooked onto a thread located on an outer wall of the CEC. According to some embodiments, the release mechanism may include a lifting of the latch by the thread due to an anti-clockwise twist of the CEC, thereby enabling release of the CEC from the adapter. According to some embodiments, the latch may have an opening hooked onto a bulge located on an outer wall of the CEC. According to some embodiments, the release mechanism may include lifting the latch, thereby freeing the bulge from the opening and enabling release of the CEC from the adapter.

According to some embodiments, the adapter may include a thread mechanism upon which the CEC may be screwed into the adapter. According to some embodiments, the adapter may include a locker extending around at least part of the adapter, thereby locking the CEC to said adapter. According to some embodiments, the release mechanism may include breaking of the locker, thereby enabling unscrewing the CEC from the adapter. According to some embodiments, the locker further may include an extension engaging with the CEC. According to some embodiments, the extension may engage with at least one wing of the CEC. According to some embodiments, the extension may include a rail in an inner wall thereof, the rail configured to match with a protruding section positioned on an outer wall of the CEC.

According to some embodiments, the locker may include at least two asymmetrical indentations in an inner wall thereof, the at least two asymmetrical indentations configured to mate with asymmetrical threads positioned on an outer wall of the CEC, thereby preventing the CEC from being unscrewed from the adapter.

According to some embodiments, the adapter may include a first secondary cone formed within a void of the adapter and the CEC may include a second secondary cone formed within a void of the CEC, wherein the first and second secondary cones are configured to mate, thereby forming an air tight passageway throughout the adapter and the CEC.

According to some embodiments, the adapter may include a feature visibly distinguishing the adapter from the CEC, such that the first configuration of the double configuration connector is visibly distinct from a second configuration of the double configuration connector.

According to some embodiments, the adapter may include a tubing interconnecting (and spacing) between the first end and the second end of said adapter. According to some embodiments, the tubing may be configured to allow undisturbed gas flow from the CEC, through the tubing to the DIC. According to some embodiments, the tubing may be a flexible tubing.

According to some embodiments, there is provided a connector for use in a respiratory gas sampling and/or delivery tubing system, the connector including a thread on an outer wall thereof; at least one wing allowing gripping the connector by a user; a first connector configuration mateable with a first device input connector (DIC); and at least one element configured to render the connector capable of connecting to an adapter, wherein connection of the connector to the adapter provides a second connector configuration to the connector, the second connector configuration mateable with a second device input connector (DIC).

According to some embodiments, the at least one element may include a position of the wings relative to a distal end of the connector. Additionally or alternatively, the at least one element may include a width of the wings. Additionally or alternatively, the at least one element may include a notch within the thread of the connector. Additionally or alternatively, the at least one element may include a protruding section on an outer wall of the connector a geometrical configuration of said thread, a bulge on an outer wall thereof, or any combination thereof. Additionally or alternatively the at least one element may include a secondary cone formed within a void of the connector.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE DRAWINGS

Some embodiments of the disclosure are described herein with reference to the accompanying figures. The description, together with the figures, makes apparent to a person having ordinary skill in the art how some embodiments of the disclosure may be practiced. The figures are for the purpose of illustrative discussion and no attempt is made to show structural details of an embodiment in more detail than is necessary for a fundamental understanding of the teachings of the disclosure. For the sake of clarity, some objects depicted in the figures are not to scale.

DETAILED DESCRIPTION

Figure 1A:
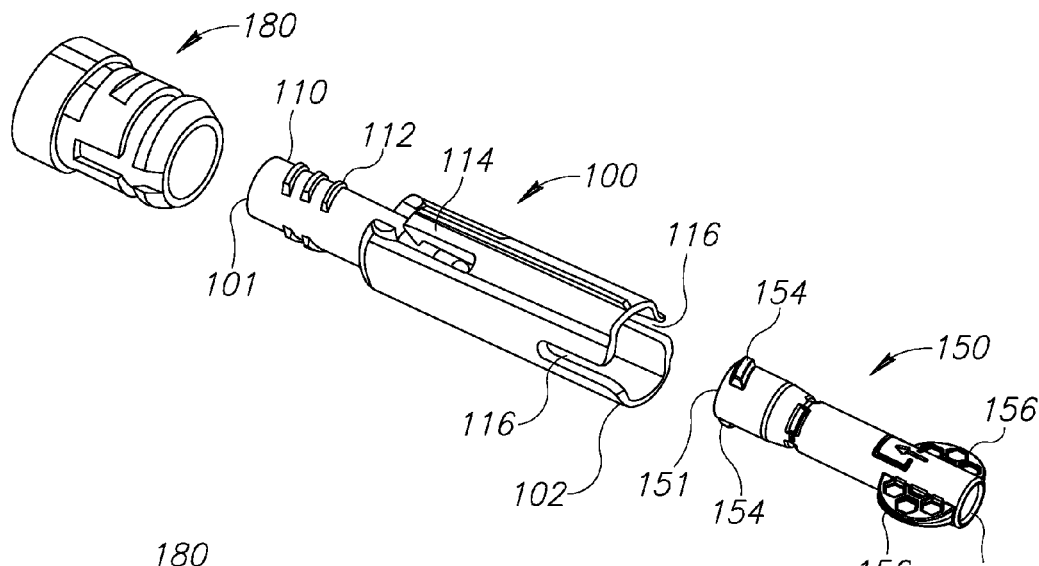
FIG. 1A and FIG. 1B show perspective views of an adapter before and after connection to a consumable end connector (CEC) and a device input connector (DIC), according to some embodiments.

In the following description, various aspects of the disclosure will be described. For the purpose of explanation, specific configurations and details are set forth in order to provide a thorough understanding of the different aspects of the disclosure. It is understood that whereas some configurations are presented in separate embodiments, combinations of embodiments or parts thereof may also be envisaged and, as such, fall within the scope of the disclosure. Similarly, it will also be apparent to one skilled in the art that the disclosure may be practiced without specific details being presented herein. Furthermore, well-known features may be omitted or simplified in order not to obscure the disclosure.

There is provided, according to some embodiments, an adapter for use in a respiratory gas sampling and/or delivery tubing system, the adapter configured to allow interconnection of a device input connector (DIC) having a first connector configuration and a consumable end connector (CEC) having a second connector configuration.

As used herein, the terms "device input connector", "DIC" and "socket" may be used interchangeably and may refer to a connector permanently fixed within a connector panel of a medical device (e.g. a capnograph) and allowing connection of a consumable (e.g. a sampling tube) having a mateable consumable connector. According to some embodiments, the DIC may have a connector configuration according to the ISO-594 standard, also referred to herein as the old standard. According to some embodiments, the DIC may have a connector configuration according to the ISO-80369 standard, also referred to herein as the new standard. According to some embodiments, the DIC may be a male connector. According to some embodiments, the DIC may be a female connector.

As used herein, the terms "consumable end connector" and "CEC" may be used interchangeably and may refer to a connector permanently fixed to or molded on a consumable such as, but not limited to, a breath sampling tube. According to some embodiments, the CEC may be a primary female connector having a form of a tapered cone. According to some embodiments, at its deepest point, the tapered cone may invert back into a secondary male section and return into a void of the primary female connector. According to some embodiments, the secondary male section (also referred to herein as a secondary cone) may include an outer wall and an inner wall, the inner wall being non-tapered, thereby forming an inner fluid flow channel, of a diameter d1, extending along the secondary male section and along the female connector. According to some embodiments, the inner fluid flow channel diameter d1 may be constant throughout the primary male connector and the primary female connector. According to some embodiments, the CEC may be a male connector. According to some embodiments, the CEC may be a female connector.

According to some embodiments, the CEC may have a connector configuration according to the ISO 80369 standard and mateable with a DIC of the ISO 80369 standard. According to some embodiments, the CEC may include one or more threads configured to allow the CEC to be screwed and/or twisted into and thus firmly attached to the ISO 80369 DIC. According to some embodiments, the CEC may include one or more wings configured to allow a firm grip by a user and hence enable the user to easily twist and/or screw the CEC into the DIC.

As used herein, the term "connector configuration" may refer to features, such as, but not limited to, size and shape of a connector. According to some embodiments, the connector configuration may provide the connector with its unique mating capabilities.

According to some embodiments, the adapter may include a first end including a first connector mateable with the DIC and a second end configured to receive at least part of the CEC. According to some embodiments, the first connector may be a male connector. According to some embodiments, the first connector may be a female connector. As used herein, the term "first end" refers to the end of the adapter connectable to a DIC and is also referred to herein as the "adapter-device end" and "A2D". As used herein, the term "second end" refers to the end of the adapter connectable to a CEC and is also referred to herein as the "adapter-consumable end" and "A2C". According to some embodiments, the CEC may be configured to be inserted essentially in its entirety within the adapter. According to some embodiments, only part of the CEC may be inserted within the adapter. According to some embodiments, the CEC may be connected to the adapter by sliding axially into the adapter. According to some embodiments, the CEC may be connected to the adapter by turning and/or twisting the CEC into the adapter. According to some embodiments, the CEC may be connected to the adapter by screwing the CEC into the adapter.

According to some embodiments, the first end (A2D) and the second end (A2C) may be interconnected by a short piece of tubing. According to some embodiments, the tubing may be configured to allow undisturbed gas flow from the CEC, through the tubing to the DIC. According to some embodiments, the tubing may be a flexible tubing.

According to some embodiments, the first connector may include means ensuring activation of the device (e.g. capnograph) when connected thereto. Additionally or alternatively. The CEC may include means ensuring activation of the device (e.g. capnograph) only when the CEC is connected to the device either directly, or through the adapter. According to some embodiments, the CEC (and/or the adapter) may include, on an end face thereof, at least two spectrally distinct reflective regions, each region configured to reflect light at a different wavelength when illuminated. According to some embodiments, activation of the medical device may be conditioned on identification of the reflected light. According to some embodiments, the CEC (and/or the adapter) may include a conductive material enabling it to close an electrical circuit, leading to the activation of the medical device, when the CEC and/or the adaptor to which it is connected is adequately connected to a device socket. According to some embodiments, the secondary male section of the female CEC may be made of a conductive material.

According to some embodiments, the adapter may include a locking mechanism configured to lock the CEC to the adapter. As used herein, the term "locking mechanism" may refer to any mechanism capable of attaching the CEC to the adapter, such that the CEC-adapter assembly acts as a single unit when handled, for example, when connecting and/or disconnecting the assembly to a DIC having a connector configuration mateable with that of the connector positioned at the first end of the adapter. According to some embodiments, the locking mechanism may be configured to reversibly lock the CEC to the adapter.

According to some embodiments, the adapter may include a release mechanism configured to release the CEC from the adapter, when needed. As used herein, the term "release mechanism" may refer to a mechanism configured to separate the CEC from the adapter, while leaving at least the CEC in its entirety. According to some embodiments, releasing the CEC from the adapter may expose the connector configuration of the CEC, thereby enabling the CEC to connect to a DIC having a connector configuration mateable with the connector configuration of the CEC (e.g. an ISO 80369 connector). According to some embodiments, the CEC may be released from the adapter by performing a minimal and simple manual action, not requiring an expert or technician, as further described herein.

According to some embodiments, the locking mechanism may be configured to prevent connection of the first connector to the DIC from activating the release mechanism. Additionally or alternatively, the locking mechanism may be configured to prevent disconnection of the first connector from the DIC from activating the release mechanism. That is, the action of screwing in the first connector (the ISO 594 connector of the adapter) into the socket of the device does not cause the minimal manual action used to release the CEC from the adapter and/or for changing the connector configuration from an ISO 594 connector to an ISO-80369 connector. Similarly, the action of unscrewing in the first connector (the ISO 594 connector of the adapter) from the socket of the device does not cause the minimal manual action used to release the CEC from the adapter and/or for changing the connector configuration from an ISO 594 connector to an ISO-80369 connector.

According to some embodiments, the connection between the adapter and the CEC may be air tight, thereby essentially preventing or at least considerably inhibiting breath samples, flowing through the CEC-adapter assembly, from leaking out thereof. According to some embodiments, an accurate position of the CEC relative to the adapter may provide an airtight adapter/CEC assembly. According to some embodiments, the tolerance between the mating parts of the adapter and the CEC may be minimal, so as provide an airtight mating.

According to some embodiments, the adapter may include a secondary cone formed within a void of the adapter, as essentially described herein. According to some embodiments, the CEC may include a secondary cone formed within a void of the adapter. According to some embodiments, the secondary cone of the adapter may mate with the secondary cone of the CEC, thereby forming an airtight passageway throughout the adapter and the second connector. According to some embodiments, the secondary cone may form an inner fluid flow channel, of a diameter $d2$, extending along the adapter. According to some embodiments, the inner fluid flow channel diameter $d2$ may be constant throughout the adapter. According to some embodiments, the inner fluid flow channel diameter $d1$ may be identical to the diameter $d1$ of the inner fluid flow channel of the CEC.

According to some embodiments, the adapter, the connector and/or the secondary cone(s) may include additional parts configured to provide airtight mating, such as, but not limited to, an O-ring. According to some embodiments, the adapter may be made from a softer, semi-flexible material for sealing purposes.

According to some embodiments, the adapter may be provided assembled to a CEC, thereby effectively functioning as a double configuration connector. Such double configuration connector enables a user, such as, for example, a hospital, to purchase a consumable connected, through its CEC, to the adapter, and thus being instantly configured to connect to a DIC having a first connector configuration (e.g. according to the ISO 594 standard). Due to the release mechanism, the double configuration connector, and thus the consumable, has an inherent ability to change its connector configurations (e.g. according to the ISO 80369 standard) by performing a minimal and simple manual action, not requiring an expert or technician. Hence, the hospital (or other end user) is not required to stock two types of consumables, i.e. one having a connector mateable with a DIC having a first connector configuration (e.g. ISO 594) and one having a connector mateable with a DIC having a second connector configuration (e.g. ISO 80369).

Alternatively, the adapter may be fixed to the medical device through the ISO 594 connector and subsequently allow connection of disposables having an ISO 80369 connector. The device adapter may include features configured to ensure adequate connection of the disposable having an ISO 80369 connector. The device adapter may further include features ensuring that once the consumable is connected to the adapter, disconnecting the consumable disconnects the adapter from the medical device. This ensures that the same adapter will not add any benefit for further use, and will not provide a means in the future for mating between any ISO 594 configuration connector and one with the new ISO 80369 configuration connector, hence rendering it useless.

According to some embodiments, the adapter may be non-reusable after activation of the release mechanism. According to some embodiments, the adapter may include at least one feature rendering it incompatible with a new CEC having a second connector configuration (e.g. ISO 80369). This may be required in order not to build up a collection of adapters that negate the reason for creating the new standard, i.e. to reduce risk.

According to some embodiments, the adapter and/or the CEC, or parts thereof, may include a feature visibly distinguishing the adapter from the CEC. As a non-limiting example, the adapter may be colored in a first color (for example the same color as used for the old ISO 594 standard connector), while the CEC connected to the adapter and having a connector configuration according to the ISO 80369 standard, will have a different color. According to some embodiments, the distinguishing feature of the CEC (e.g. its color) may be invisible when the CEC is connected to and/or within the adapter. According to some embodiments, the distinguishing feature of the CEC (e.g. its color) may be exposed/revealed upon release of the CEC from the adapter.

According to some embodiments, the second end of said adapter may include at least one slot configured to slidingly receive a wing of the CEC. According to some embodiments, the adapter may include two or more slots, positioned such as to enable two or more wings on the CEC to axially slide into the slots, i.e. without being screwed and or twisted. According to some embodiments, the width of the slot(s) may be predetermined so as only to allow a CEC with wings with a width at or below the width of the slots to slide into the slots. Similarly, according to some embodiments, the width of the slot(s) may be predetermined so as only to allow a CEC with wings above a predetermined width to be retained within the slots. According to some embodiments, the length of the slots may be so that the CEC having its wings positioned at a predetermined distance from the distal end of the CEC, may slide into the adapter and be connected thereto. According to some embodiments, the shape of the slot(s) may be such that only a CEC with wings having a shape fitting the slots, slide therein. According to some embodiments, the plane of the slots on the connector may be such that the CEC can only be connected if its wings are in the same plane as the slots. According to some embodiments, the orientation of the slots may be such that the CEC can only be connected if its wings have a same orientation. It is thus understood that the wings can have a size, a position relative to the distal end of the CEC, or an orientation rendering it uniquely compatible with the adapter. Furthermore, if the CEC has more than two wings, their orientation at any given angle relative to each other may serve as a feature ensuring a unique adapter-CEC assembly.

According to some embodiments, the locking mechanism may include one or more hooks configured to hook onto the thread located on an outer surface of the CEC. According to some embodiments, the hook may hook onto the thread from a distal side thereof, i.e. from the side of the thread close to the distal end of the connector (i.e. the end of the connector furthest away from the consumable). According to some embodiments, the hook may hook onto the thread from a proximal side thereof, i.e. from the side of the thread further away from the distal end of the connector. According to some embodiments, the one or more hooks can be displaced outwards when sliding the CEC into the adapter. According to some embodiments, the one or more hooks can hook onto the CEC after the thread of the CEC has passed the hook. It is thus understood that although the CEC includes a female side (of the ISO 80369 standard) with threads, and will thread accordingly with a compliant male configuration of the same standard, it does not use the thread in order to mate with the adapter. Instead, the CEC slides in axially, with no turning motion into the second end of the adapter, until the hook has hooked on to secure the CEC thread. Upon connection of the CEC to the adapter, the user may grip the wings to turn the first end of the adapter (the A2D end) into the device. Since the wings are lodged within the slots, the CEC-adapter assembly may act as a single unit. Similarly, the CEC-adapter assembly may be disconnected from the DIC by gripping the wings, lifting the hook and pulling out the assembly. Since the wings are locked within the slots, the assembly works as a single unit and disconnects from the device.

According to some embodiments, the release mechanism may include an outward displacement of the hook from the thread, thereby enabling pulling out the CEC from the adapter. Thus, if the user (e.g. the hospital) uses medical devices, such as a capnograph having a DIC compatible with the ISO 80369 standard, then the user may lift the hook, and remove the CEC from the adapter (with the ISO 594 standard connector) by gripping the wings. Since the CEC is in accordance with the ISO 80369 standard it will fit the ISO 80369 DIC.

According to some embodiments, when there will be sufficient devices in the field having an ISO 80369 standard DIC, then consumables having an ISO 80369 standard CEC may be provided without being connected to the adapter, i.e. a consumable with a single configuration connector. Importantly, the single configuration connector may have a different number of wings or having the wings positioned differently, so that while being in compliance with the ISO 80369 standard, they may not fit the adapter.

According to some embodiments, the locking mechanism may include at least one latch, configured to latch onto the thread of the CEC. According to some embodiments, at least part of the latch may include a first segment and a second segment. According to some embodiments, the first and second segments may be upper and lower segments. According to this embodiment, the CEC may be connected to the second end of the adapter by sliding into the adapter, rather than by means of twisting and/or screwing the threads against an opposing compatible thread on the adapter.

According to some embodiments, the latch may include a protrusion in an inner wall thereof, the protrusion may be configured to be received within a notch formed within a thread of the CEC. Thus, in order to accept the CEC, as well as to align correctly between the two mating parts, the notch set within the CEC thread length may receive the protrusion formed in the locking mechanism of the adapter, thereby acting as a lock and key mechanism (without negating compliance with the ISO80369 standard).

Upon connection of the CEC to the adapter, the user may grip the wings to screw the first end of the adapter (the A2D end) into the device. Since the latch hooks onto the CEC threads, the CEC-adapter assembly may act as a single unit. Similarly, the CEC-adapter assembly may be disconnected from the DIC by gripping the wings, and screwing or pulling out the assembly. Since the latch is hooked on to the CEC threads, the assembly disconnects from the device as a single unit.

According to some embodiments, the latch may be pushed out transversely while pushing in the CEC, for example, by not creating a full annular part, i.e. dividing the latch into first and second segments and/or using more than one latch.

According to some embodiments, the release mechanism may include a lifting of the latch by the thread, when the CEC is twisted in a counter-clockwise direction relative to the adapter. Thus, in order to remove the adapter from the CEC, the user may twist the CEC, while gripping in one hand the wings, and the other hand the adapter. According to some embodiments, at least part of the latch may include a thinned wall. According to some embodiments, at least part of the latch may include a wall made of a flexible material. Such thinned and/or flexible wall may enable the CEC thread to lift up the latch and thus permit the release of the CEC from the adapter, during the twisting motion of the CEC. According to some embodiments, the distance between the first and second segments of the latch (or the distance between two separate latches) may be longer than the length of the thread, thereby enabling the thread to slide out between the first and second segments of the latch after twisting the CEC relative to the adapter. Thus, if the user (e.g. the hospital) uses medical devices, such as a capnograph having a DIC compatible with the ISO 80369 standard, then the user may twist out the CEC from the latch, and remove the CEC from the adapter by gripping the wings in one hand and the adapter in the second hand. Since the CEC is in accordance with the ISO 80369 standard it will fit the ISO 80369 DIC. According to some embodiments, the force required to lift the latch in the counter-clockwise direction may be designed to be larger than the torque required to remove the CEC-adapter assembly from the DIC.

According to some embodiments, the adapter may include gripping positions on the adapter. According to some embodiments, the gripping positions may include wings. According to some embodiments, the wings may be used to grip firmly the adapter providing torque and moment when twisting the adapter into an installed device. According to some embodiments, when removing the adapter from the device, the gripping wings may be used to provide the torque required for removal of the CEC from the adapter. According to some embodiments, the wings may be placed on a positon of the adapter above the thinned and/or flexible wall, such that force used to detach the CEC-adapter assembly from the DIC pushes down the thinned and/or flexible wall, thereby preventing the release of the CEC from the adapter.

According to some embodiments, when there will be sufficient devices in the field having an ISO 80369 standard DIC, consumables having an ISO 80369 standard CEC may be provided without being connected to the adapter, i.e. a consumable with a single configuration connector. Importantly, the single configuration connector may not include a notch in its thread and will therefore not be compatible with the adapter having a protrusion in an inner wall of its latch.

According to some embodiments, the adapter may be built from two or more parts, the basic adapter part and a second part, that is used to lock the CEC in position. According to some embodiments, the second part may be a locker, such as but not limited to a snap-on locker, configured, at least partially, to extend around the adapter. According to some embodiments, the attachment of the CEC to the adapter may be performed without the second adapter part. According to some embodiments, the connection of the CEC to the adapter may be performed while using the standard twisting and screwing functionality of the thread on the CEC. Hence, the adapter may, according to this embodiment include a mateable thread allowing the CEC to be screwed into the adapter. According to some embodiments, the locker, serving as the locking mechanism, may prevent the screwing functionality from occurring, thereby locking the CEC to the adapter. According to some embodiments, the locker may be welded on the adapter after the CEC has been screwed into the adapter. According to some embodiments, the locker may be designed such that when the CEC is screwed into the adapter, it lifts the ends of the locker (e.g. the snap in section thereof), such that the threads of the CEC can pass the locker and subsequently be locked within the adapter.

According to some embodiments, the locker may have a protrusion in an inner wall thereof. The protrusion may be received within an opening or indentation in an outer wall of the adapter, thereby preventing the CEC from being unscrewed from the adapter.

Upon connection of the CEC to the adapter, the user may grip the wings to screw the first end of the adapter (the A2D end) into the device. Since the locker locks the CEC to the adapter, the CEC-adapter assembly may act as a single unit. Similarly, the CEC-adapter assembly may be disconnected from the DIC by gripping the wings, and screwing or pulling out the assembly. Since the locker locks the CEC to the adapter, the assembly disconnects from the device as a single unit.

According to some embodiments, the release mechanism may include breaking of the locker, thereby enabling unscrewing the CEC from the adapter. For example, the locker may include a line of narrower wall thickness, causing the locker to break along the line when removed, thereby rendering the locker useless after removal. It is thus understood, that the CEC connected to the adapter and forming a double configuration connector therewith, may be a basic ISO 80369 connector. However, connection of a new ISO 80369 CEC is impossible since a firm attachment of the CEC to the adapter may only be achieved when an intact locker locks around the CEC-adapter assembly.

According to some embodiments, the locker may include an extension configured to lock the wings of the CEC, thereby securing the CEC-adapter assembly. According to some embodiments, the wings may be positioned relatively close to the distal end of the CEC, so as not to create a too long extension. According to some embodiments, the wings may be positioned anywhere along $2/3$ of the CEC closest to the distal end, such as anywhere along $1/2$ of the CEC closest to the distal end or such as anywhere along $1/3$ of the CEC closest to the distal end. Each possibility is a separate embodiment.

According to some embodiments, the extension may include a limiting ring, configured to extend, at least partially, around at least part of the CEC. According to some embodiments, the limiting ring may include at least one indentation/rail in an inner wall thereof, the rail configured to match with at least one protruding section positioned on an outer wall of the CEC. According to some embodiments, the protruding section may be a protruding ring. According to some embodiments, the limiting ring and/or the protruding ring may not be full rings. For example, the rail of the adapter may be made of three (equally) spaced out rails, and the CEC may have three similar limiting protruding sections fitting between the rails of the adapter, thereby generating a lock and key formation.

It is understood that the protruding section(s) on the CEC may serve as the feature rendering a CEC, devoid of such, incompatible with the adapter. Thus, when there will be sufficient devices in the field having an ISO 80369 standard DIC, consumables having an ISO 80369 standard CEC may be provided without being connected to the adapter, i.e. a consumable with a single configuration connector. Importantly, the single configuration connector may not include a protruding section and will therefore not be compatible with the adapter having a locker with a rail.

According, to some embodiments, the adapter may be built from two or more parts, the basic adapter part and a second part, a locker, used to lock the CEC within the adapter, thus serving as the locking mechanism. According to some embodiments, the adapter may include a protrusion in an outer wall thereof. According to some embodiments, the protrusion may be sized and shaped to be received within an opening or indentation in an inner wall of the locker.

According, to some embodiments, the locker may include at least two asymmetrical indentations in an inner wall thereof, the at least two asymmetrical indentations configured to mate with asymmetrical threads positioned on an outer wall of the CEC. According to some embodiments, for connection of the CEC to the adapter, the CEC is passed through the locker and then screwed into the adapter (though a design in which the CEC is not screwed in and in which the threads are not used when connected with the adapter may also be applicable). According to some embodiments, the locker may be welded on the adapter after the CEC has been connected to the adapter. According to some embodiments, the locker may include slots configured to receive the wings of the CEC during the CEC-adapter assembly.

Upon connection of the CEC to the adapter, the user may grip the wings to screw the first end of the adapter (the A2D end) into the device. Since the locker locks the CEC to the adapter, the CEC-adapter assembly acts as a single unit. Similarly, the CEC-adapter assembly may be disconnected from the DIC by gripping the wings, and screwing or pulling out the assembly. Since the locker locks the CEC to the adapter, the assembly disconnects from the device as a single unit.

According to some embodiments, the release mechanism includes releasing the locker from the adapter, for example, by screwing the locker of the adapter. According to some embodiments, removal of the locker may cause its breakage. Thus, if the user (e.g. the hospital) uses medical devices, such as a capnograph having a DIC compatible with the ISO 80369 standard, then the user may screw off the locker, and remove the CEC from the adapter (with the ISO 594 standard connector). Since the CEC is in accordance with the ISO 80369 standard it will fit the ISO 80369 DIC.

It is understood that the asymmetrical position of the treads on the CEC may serve as the feature rendering the CEC compatible with the adapter. Thus, when there will be sufficient devices in the field having an ISO 80369 standard DIC, consumables having an ISO 80369 standard CEC may be provided without being connected to the adapter, i.e. a consumable with a single configuration connector. Importantly, the single configuration connectors include regular, symmetrically positioned threads and will therefore not be compatible with the adapter.

According to some embodiments, the locking mechanism of the adapter may include one or more latches or tongues having at least one opening. According to some embodiments, the at least one opening may be configured to hook onto at least one bulge located on an outer wall of the CEC. According to some embodiments, the CEC may be slidingly/axially inserted into the adapter without requiring screwing and/or twisting, while lifting the tongue. According to some embodiments, the tongue may be flexible (due to design or material), thereby enabling it to lift to accommodate the protrusion.

Upon connection of the CEC to the adapter, the user may grip the wings to screw the first end of the adapter (the A2D end) into the device. Since the tongue hooks onto the bulge on the CEC, the CEC-adapter assembly acts as a single unit. Similarly, the CEC-adapter assembly may be disconnected from the DIC by gripping the wings, and unscrewing or pulling out the assembly. Since the tongue hooks onto the bulge on the CEC, the assembly disconnects from the device as a single unit.

According to some embodiments, the CEC may include two or more bulges, such as 2, 3, 4, 5 or more protrusions. Each possibility is a separate embodiment. According to some embodiments, the two or more bulges may be positioned on opposite sides of the CEC. According to some embodiments, the distance between a top end of the first protrusion and a top end of the second protrusion may be larger than the internal diameter of the adapter. According to some embodiments, the adapter may include at least two tongues. According to some embodiments, at least one of the tongues may include an extension configured to allow gripping thereof by a user. According to some embodiments, only one of the tongues may include an extension configured to allow gripping thereof by a user. According to some embodiments, the diameter of the adapter in an orientation perpendicular to the tongue is larger than the diameter in the plane of the tongue, thereby allowing accommodation of the CEC threads.

According to some embodiments, the first bulge on the CEC may be shaped with a sharp angle (e.g. approximately 90°). According to some embodiments, the long tongue may be configured to hook on the sharp angled bulge. According to some embodiments, the second bulge on the CEC may have an angle above 90° (e.g. 120°) making it relatively easy to release when the tongue is raised. According to some embodiments, the end of the (long) tongue may be shaped to accommodate gripping.

Upon connection of the CEC to the adapter, the user may grip the wings to screw the first end of the adapter (the A2D end) into the device. Since the locker locks the CEC to the adapter, the CEC-adapter assembly acts as a single unit. Similarly, the CEC-adapter assembly may be disconnected from the DIC by gripping the wings, and unscrewing or pulling out the assembly. Since the locker locks the CEC to the adapter, the assembly disconnects from the device as a single unit.

According to some embodiments, the release mechanism may include a lifting of the tongue (above the sharp angled bulge), thereby enabling the CEC to be pulled out. Thus, if the user (e.g. the hospital) uses medical devices, such as a capnograph having a DIC compatible with the ISO 80369 standard, then the user may lift the tongue, and remove the CEC from the adapter (with the ISO 594 standard connector). Since the CEC is in accordance with the ISO 80369 standard it will fit the ISO 80369 DIC.

It is understood that the bulge on the outer wall of the CEC may serve as the feature rendering the CEC compatible with the adapter. Thus, when there will be sufficient devices in the field having an ISO 80369 standard DIC, consumables having an ISO 80369 standard CEC may be provided without being connected to the adapter, i.e. a consumable with a single configuration connector. Importantly, the single configuration connectors are devoid of bulges and will therefore not be compatible with the adapter.

As used herein the term "distal end" when referring to the CEC may refer to the end of the CEC furthest away from the consumable (e.g. breath sampling tube).

As used herein the term "proximal end" when referring to the CEC may refer to the end of the CEC closest to the consumable (e.g. breath sampling tube).

As used herein, the terms "one or more" and "at least one" may interchangeably be used and may refer to 1, 2, 3, 4, 5 or more of the item to which it refers. Each possibility is a separate embodiment. As used herein, the terms "two or more" and "at least two" may interchangeably be used and may refer to 2, 3, 4, 5 or more of the item to which it refers. Each possibility is a separate embodiment.

Reference will now be made to the figures. The figures are directed to several alternative adapters and/or double configuration connectors. It is obvious that each defines a general concept, where the proposed design is an example of a group of solutions and embodiments. Further, features of one concept may be added to a second concept in order to enhance its functionality and compliance with the defined requirements.

Figure 1B:
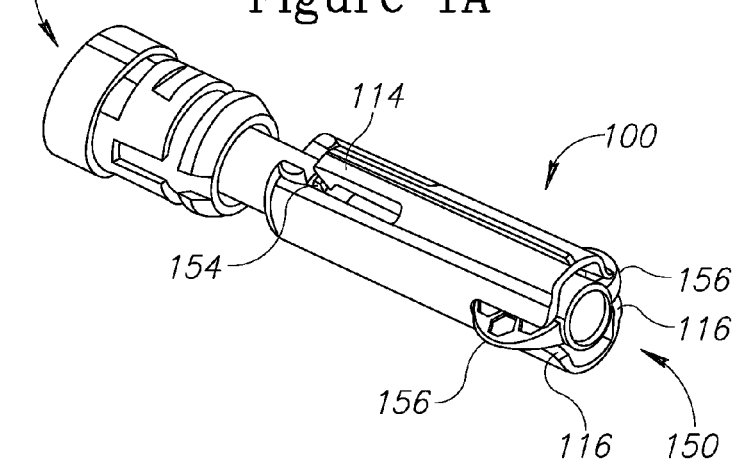

Reference is now made to FIG. 1A-FIG. 1B which show views of an adapter 100 before and after connection to a consumable end connector (CEC) 150 and a device input connector (DIC) 180, according to some embodiments. DIC 180, which conforms to the old (ISO 594) standard, is normally incorporated and fixed within a device connector panel (not shown). CEC 150 complies with the new ISO 80369 standard and is generally an integral part of a capnograph sampling line and patient interface (not shown). CEC 150 includes, at a distal end 151 thereof, threads 154, used for firm connection to a mating connector of the same standard. At its proximal end 152, CEC 150 includes wings 156, used for providing a firm grip to the user and ability to twist easily for mating purposes.

Adapter 100 includes a first end (A2D) 101 with a first connector 110 having a first connector configuration, here a connector configuration according to the ISO 594 standard, enabling adapter 100 to be screwed into DIC 180 using threads 112. A second end (A2C) 102 of adapter 100 is configured to receive CEC 150. According to this embodiment, adapter 100 includes slots 116 sized and shaped to receive wings 156. It is understood that wings 156 may have a size, position and/or orientation on CEC 150 different from typical ISO 80369 connectors, thereby dictating the position and length of slots 116 on adapter 100 and making the connection of CEC 150 to adapter 100 unique. In addition, CEC 150 may include more than two wings orientated at any given angle relative to each other. Adapter 100 further includes a hook 114 configured to hook onto threads 154 of CEC 150, thereby locking CEC 150 within adapter 100. Hook 114 can be displaced outwards when sliding CEC 150 into adapter 100, so as to hook onto CEC 150 after threads 154 have passed hook 114. It is thus understood that although CEC 150 is a female connector compliant with the ISO 80369 standard, threads 154 are not used to mate with adapter 100. Instead, CEC 150 slides axially, with no turning motion into A2C 102, until hook 114 is secured on threads 154 of CEC 150.

Upon connection of CEC 150 into adapter 100, as depicted in FIG. 1B, the assembly serves as a single unit that may be screwed in and out of DIC 180 without being disassembled. The assembly (CEC 150 inserted into adapter 100) has an inherent ability to become either one of the connector configurations, by performing a minimal and simple manual action (not requiring an expert or technician). The hospital (or other end user) will therefore not be required to stock two types of consumables, i.e. one ending with an ISO 594 configuration connector and one with the new ISO 80369 configuration connector. Preferably, the consumable may, during the first few years of the transfer period, be marketed and distributed where it is ready for connection with an ISO 594 socket (the majority of devices in field), and where to use it with the new ISO 80369 compatible device, the minimal manual action is required. That is, the double configuration connector is ready to connect to a DIC having an old connecter configuration through first connector 110 of adapter 100. However, if new devices having sockets compatible with the ISO 80369 standard are used, hook 114 may be lifted, thereby enabling CEC 150 to be removed from adapter 100, by gripping wings 156 and pulling out CEC 150 from A2I 102. Since CEC 150 is in compatible with the ISO 80369 standard, it will fit the ISO 80369 socket of the device.

After removal of CEC 150 from adapter 100, adapter 100 will not be usable again with any new standard ISO 80369 configuration connector that is not of the type that comes with the adapter (which anyway comes with an adapter). The single use is achieved by the unique size, position and/or orientation of wings 156 on CEC 150, preventing connection of a new ISO 80369 connector having standard wing size, position and/or orientation. Accordingly, saving adapter 100 will not add any benefit for further use, and will not serve as means for future mating between DIC 180 and a new ISO 80369 connector, hence rendering adapter 100 useless after its first use. It is understood to one of ordinary skill in the art that such single use limitation is important in order to prevent buildup of a collection of adapters that negate the reason for creating the new standard, i.e. to reduce risk.

When devices with the new ISO 80369 configuration socket become abundant, marketing of consumables that are compatible with the new standard device sockets can be initiated. However, in order to ensure that these single configuration consumables do not connect with adapter 100, the consumables may be provided with an ISO 80369 connector having wings with a different size, position and/or orientation, rendering it incompatible with adapter 100, while avoiding impairment of its compliance with the new standard.

Figure 1C:
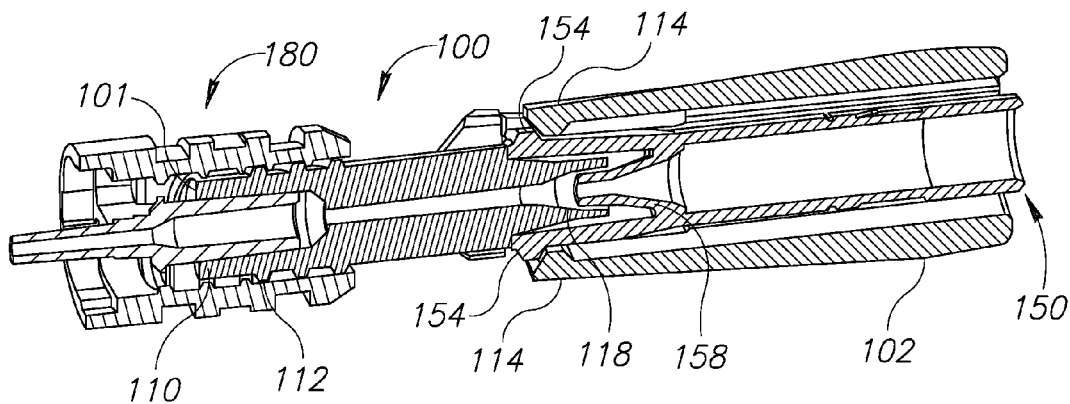
FIG. 1C shows a cross section of the adapter connected to a CEC and a DIC, according to some embodiments.

FIG. 1.C shows a cross section of adapter 100 connected to CEC 150 and to DIC 180, according to some embodiments. CEC 150 is inserted, essentially in its entirety, into adapter 100 such that hook 114 hooked onto CEC 150 serves as a stopper on threads 154 preventing the withdrawal of CEC 150 from adapter 100. Furthermore, adapter 100 includes a secondary cone 118 configured to mate with a secondary cone 158 of CEC 150, thereby ensuring an airtight passageway with minimal disturbances to flow, from CEC 150 to adapter 100 and further to DIC 180, once securely assembled.

Figure 2A:
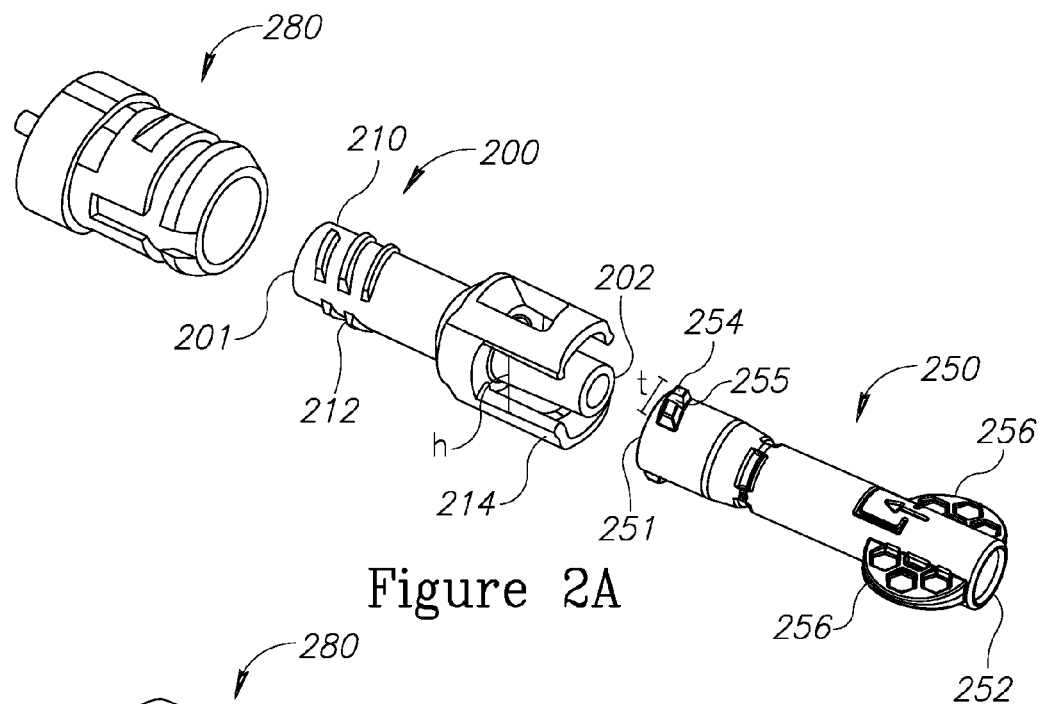
FIG. 2A and FIG. 2B show perspective views of an adapter before and after connection to a CEC and a DIC, according to some embodiments.
Figure 2B:
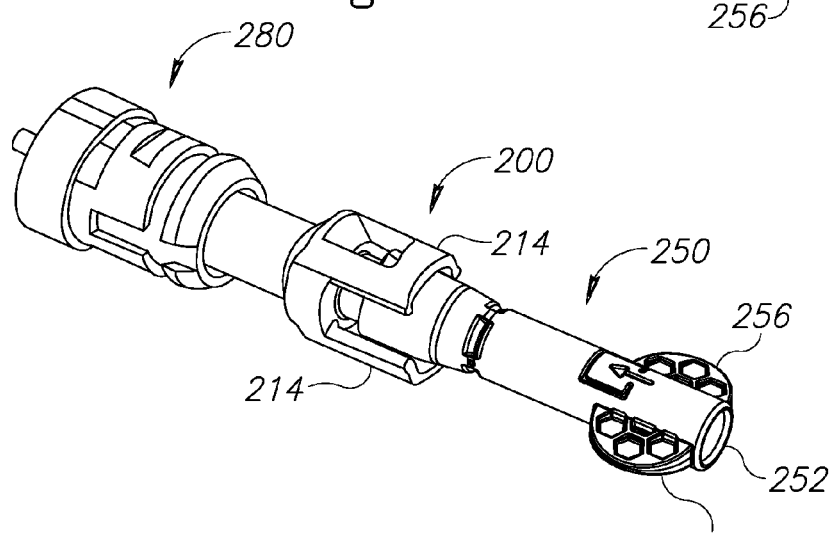

Reference is now made to FIG. 2A-FIG. 2B which show views of an adapter 200 before and after connection to a consumable end connector (CEC) 250 and a device input connector (DIC) 280, according to some embodiments. DIC 280, which conforms to the old (ISO 594) standard is normally incorporated and fixed within the device connector panel (not shown). CEC 250 complies with the new ISO 80369 standard and is generally an integral part of a capnograph sampling line and patient interface (not shown). CEC 250 includes, at a distal end 251 thereof, threads 254, used for firm connection to a mating connector of the same standard. At a proximal end 252 thereof, CEC 250 includes wings 256, used for providing a firm grip to the user and ability to twist easily for mating purposes.

Figure 2C:
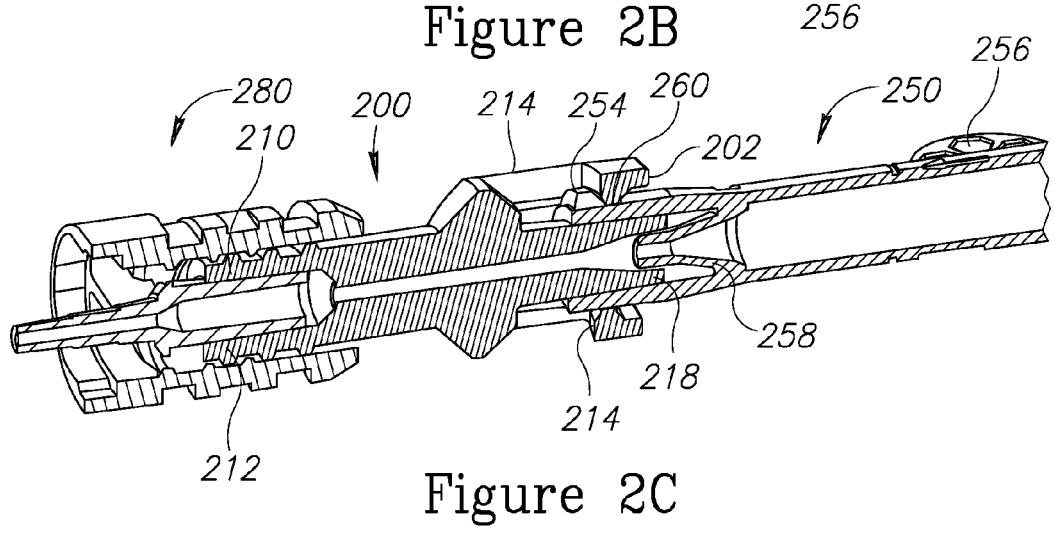
FIG. 2C shows a cross section of an adapter connected to a CEC and a DIC, according to some embodiments.

Adapter 200 includes a first end (A2D) 201 with a first connector 210 having a first connector configuration, here a connector configuration according to the ISO 594 standard, enabling adapter 200 to be screwed into DIC 280 using threads 212. A second end (A2C) 202 of adapter 200 is configured to receive CEC 250. According to this embodiment, adapter 200 includes latches 214 configured to latch onto at least one of threads 254 of CEC 250, thereby locking CEC 250 to adapter 200. For connection, at least one of latches 214 is displaced outwards enabling CEC 250 to slide into A2C 202 until latches 214 have latched onto thread 254 of CEC 250. At least one of latches 214 include a protrusion 260 (shown in FIG. 2C) configured to be received within a groove 255 formed in at least one of threads 254, thereby ensuring correct alignment between CEC 250 and adapter 200.

Upon connection of CEC 250 into adapter 200, as depicted in FIG. 2B, the assembly serves as a single unit that may be screwed in and out of DIC 280 without being disassembled.

The double configuration assembly (CEC 250 inserted into adapter 200) has an inherent ability to become either one of the connector configurations, by performing a minimal and simple manual action (not requiring an expert or technician). The hospital (or other end user) will therefore not be required to stock two types of consumables, i.e. one ending with an ISO 594 configuration connector and one with the new ISO 80369 configuration connector. It is preferable, that the consumable during the first few years of the transfer period be marketed and distributed where it is ready for connection with the installed base, ISO 594 socket (the majority of devices in field), and where to use it with a new ISO 80369 compatible device, the minimal manual action is required. That is, the double configuration connector is ready to connect to a device socket having an old connecter configuration through first connector 210 of adapter 200. However, if the device has a socket compatible with the ISO 80369 standard, at least one of latches 214 may be pushed out transversely, thereby enabling CEC 250 to be removed from adapter 200, by gripping wings 256 and pulling out CEC 250 from A2I 202. Latches 214 do not create a full annular part. Thus, CEC 250 may, when twisted counter-clockwise (unlike when securing the assembly into DIC 280 through connector 210), cause a lifting up of at least one of latches 214, thereby facilitating release of CEC 250 from adapter 210. According to some embodiments, part of at least one of latches 214, (for example the upper one of latches 214) may have a thinned wall and/or be made of a flexible material, thereby easing the lifting of latches 214 by threads 254. Moreover, the distance h between latches 214 is larger than the length t of threads 254; thereby enabling an upper one of threads 254 to slide out between latches 214.

According to some embodiments, adapter 200 may also include gripping features such as, for example, wings (not shown). Such wings have two purposes; firstly they may be used to firmly grip adapter 200 providing torque and moment when twisting the adapter 210 in (or out) of DIC 280 and secondly, if the wings are placed above the thinned and/or flexible wall, the counter-clockwise force used to detach the single unit assembly (CEC 250 locked to adapter 200) will push down the thinned wall, preventing the assembly to separate into its constituting adapter 200 and CEC 250. Similarly, when connecting adapter 200 to DIC 280 through connector 210, the clockwise screwing of the assembly does not cause the assembly to separate into its constituting adapter 200 and CEC 250, as threads 254 meet a thickened wall of latches 214, preventing the disassembly. In addition, the force required to lift latches 214 is designed to be much larger than the torque required for removing adapter 200 from DIC 280.

After removal of CEC 250 from adapter 200, adapter 200 will not be usable again with any new standard ISO 80369 configuration connector that is not of the type that comes with the adapter (which anyway comes with an adapter). This is achieved since connectors having a full length thread devoid of groove 255 will be prevented from being connected to adapter 200. Accordingly, saving adapter 200 will not add any benefit for further use, and will not serve as a means for future mating between DIC 280 and a new ISO 80369 connector, hence rendering adapter 200 useless after its first use. It is understood to one of ordinary skill in the art that such single use limitation is important in order to prevent buildup of a collection of adapters that negate the reason for creating the new standard, i.e. to reduce risk.

When devices with the new ISO 80369 configuration socket become abundant, marketing of consumables that are compatible with the new standard device sockets can be initiated. However, in order to ensure that these single configuration consumables do not connect with adapter 200, the consumables may be provided devoid of groove 255, thereby preventing them from connecting to adapter 200.

FIG. 2.C, shows a cross section of adapter 200 connected to CEC 250 and to DIC 280, according to some embodiments. CEC 250 is connected to adapter 200 (without being inserted therein) to a point allowing latches 214 to be hooked onto threads 254, thereby preventing of CEC 250 from being pulled out of adapter 200. Furthermore, adapter 200 includes a secondary cone 218 configured to mate with a secondary cone 258 of CEC 250, thereby ensuring an air tight passageway with minimal disturbances to flow from CEC 250 to adapter 200 and further to DIC 280, once securely assembled.

Figure 3A:
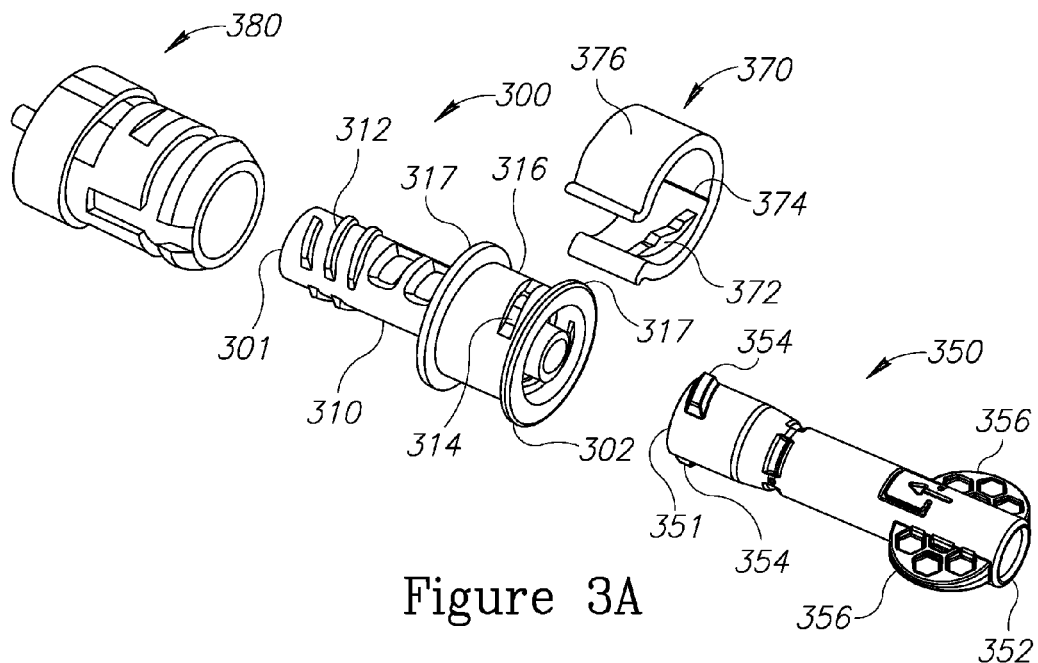
FIG. 3A and FIG. 3B show perspective views of an adapter before and after connection to a CEC and a DIC, according to some embodiments.
Figure 3B:
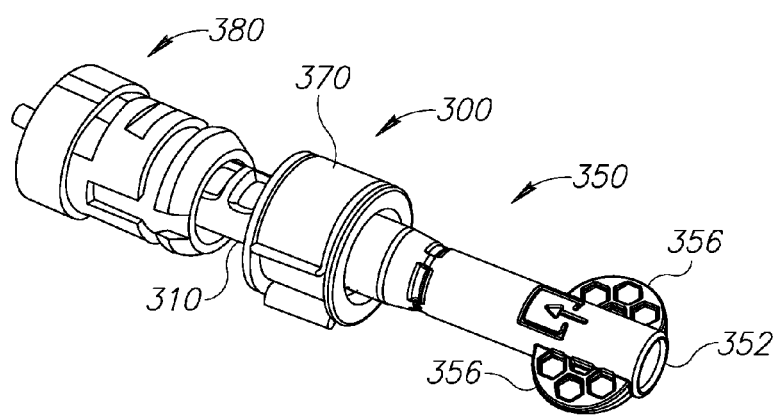

Reference is now made to FIG. 3A-FIG. 3B, which show views of an adapter 300 before and after connection to a consumable end connector (CEC) 350 and a device input connector (DIC) 380, according to some embodiments. DIC 380, which conforms to the old (ISO 594) standard, is normally incorporated and fixed within a device connector panel (not shown). CEC 350 complies with the new ISO 80369 standard and is generally an integral part of a capnograph sampling line and patient interface (not shown). CEC 350 includes, at a distal end 351 thereof, threads 354, used for firm connection to a mating connector of the same standard. At its proximal end 352, CEC 350 includes wings 356, used for providing a firm grip to the user and ability to twist easily for mating purposes.

Figure 3C:
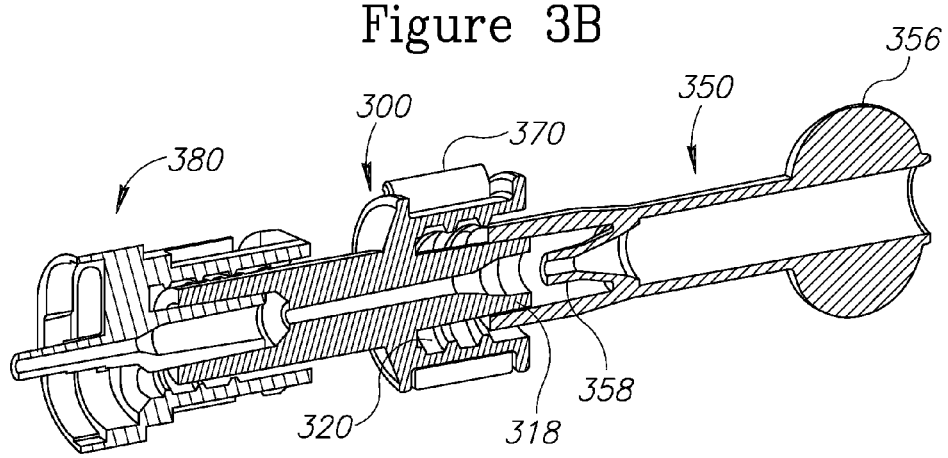
FIG. 3C shows a cross section of an adapter connected to a CEC and a DIC, according to some embodiments.

Adapter 300 includes a first end (A2D) 301 with a first connector 310 having a first connector configuration, here a connector configuration according to the ISO 594 standard, enabling adapter 300 to be screwed into DIC 380 using threads 312. A second end (A2C) 302 of adapter 300 is configured to receive CEC 350. According to this embodiment, adapter 300 further includes a locker, separate from adapter 300, such as snap-on locker 370 configured to be snapped around an indented wall 316 of the adapter, between limiting annular rings 317. Attachment (and detachment) of CEC 350 is performed without snap-on locker 370, and is done by twisting and/or screwing threads 354 of CEC 350 into mating thread mechanism 320 (shown in FIG. 3C) of adapter 300. After CEC 350 has been screwed into adapter 300, snap-on locker 370 is snapped around adapter 300, thereby preventing CEC 350 from being unscrewed from adapter 300. Snap-on locker 370, has a protrusion 372 intended to perform the locking feature when placed snapped around adapter 300, via an opening 314 in indented wall 316 of adapter 300 configured to receive protrusion 372. According to some embodiments, snap-on locker 370 may include an extension (not shown) configured to lock wings 356 of CEC 300. Wings 356 would preferably be positioned at larger than usual distance from proximal end 352 of CEC 350 and thus closer to the extension in order for the latter not to be too long.

Upon connection of CEC 350 into adapter 300 and lockage of the assembly by snapping on snap-on locker 370, as depicted in FIG. 3B, the assembly serves as a single unit that may be screwed in and out of DIC 380 without being disassembled. The stability of the assembly (CEC 350 connected to adapter 300) by the addition of the extension to snap-on locker 370 configured to lock wings 356 of CEC 300.

The assembly (CEC 350 connected to adapter 300) has an inherent ability to become either one of the connector configurations, by performing a minimal and simple manual action (not requiring an expert or technician). The hospital (or other end user) will therefore not be required to stock two types of consumables, i.e. one ending with an ISO 594 configuration connector and one with the new ISO 80369 configuration connector. Preferably, the consumable may, during the first few years of the transfer period, be marketed and distributed where it is ready for connection with an ISO 594 socket (the majority of devices in the field), and where to use it with the new ISO 80369 compatible device, the minimal manual action is required. That is, the double configuration connector is ready to connect to a DIC having an old connecter configuration through first connector 310 of adapter 300. However, if new devices having sockets compatible with the ISO 80369 standard are used, snap-on locker 370 may be removed, thereby enabling CEC 350 to be screwed out of adapter 300. Since CEC 350 is incompatible with the ISO 80369 standard it will fit the ISO 80369 socket of the device.

According to some embodiments, snap-on locker 370 may be construed such that when removing it from adapter 300 it breaks. For example, snap-on locker 370 may include a breakage line, such as breakage line 374 in a wall 376, made of a thinner wall thickness. It is understood to one of ordinary skill in art that breakage of snap-on locker 370 renders it useless after removal.

According to some embodiments, after removal of CEC 350 from adapter 300, adapter 300 will not be usable again with any new standard ISO 80369 configuration connector that is not of the type that comes with the adapter (which anyway comes with an adapter), as adaptor 300, devoid of locker 370, will fail to retain connector 350 connected thereto. Accordingly, saving adapter 300 will not add any benefit for further use, and will not serve as a means for future mating between DIC 380 and a new ISO 80369 connector, hence rendering adapter 300 useless after its first use. It is understood to one of ordinary skill in the art that such single use limitation is important in order to prevent buildup of a collection of adapters that negate the reason for creating the new standard, i.e. to reduce risk.

When devices with the new ISO 80369 configuration socket become abundant, marketing of consumables that are compatible with the new standard device sockets can be initiated. Preferably, the consumables will be provided with an ISO 80369 connector having wings at its usual proximal position.

FIG. 3.C shows a cross section of adapter 300 connected to CEC 350 and to DIC 380, according to some embodiments. CEC is screwed into adapter 300 and subsequently locked thereto by snapping on snap-on locker 370, thereby preventing CEC 350 from being screwed out of adapter 300. Furthermore, adapter 300 includes a secondary cone 318 configured to mate with a secondary cone 358 of CEC 350, thereby ensuring an air tight and passageway with minimal disturbances to flow, from CEC 350 to adapter 300 and further to DIC 380, once securely assembled.

Figure 4A:
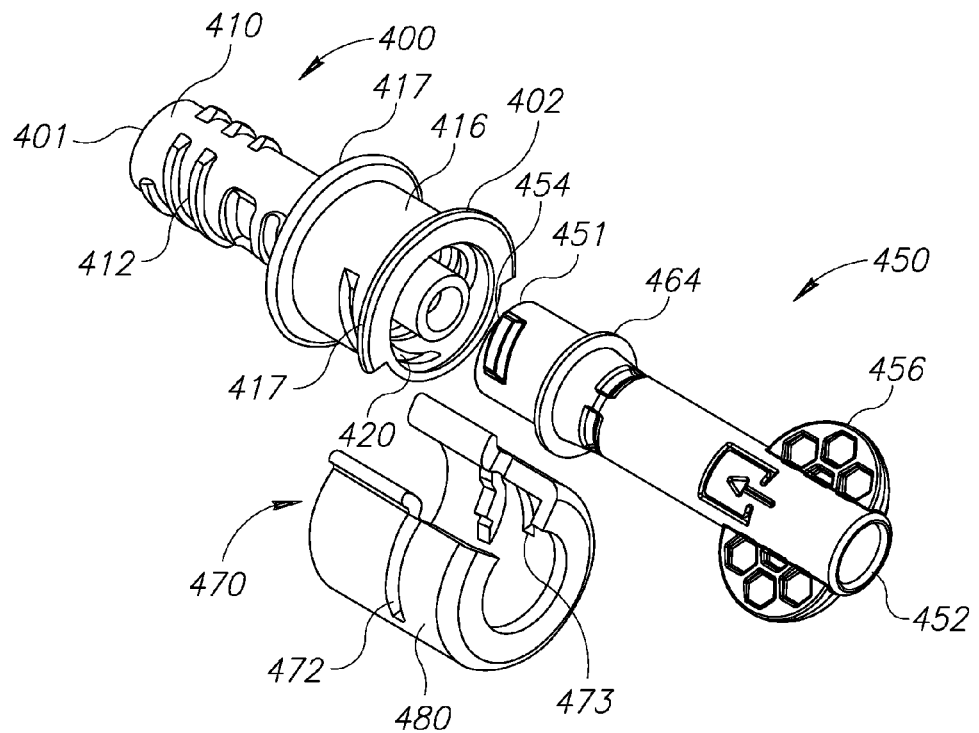
FIG. 4A and FIG. 4B show perspective views of an adapter before and after connection to a CEC, respectively, according to some embodiments.
Figure 4B:
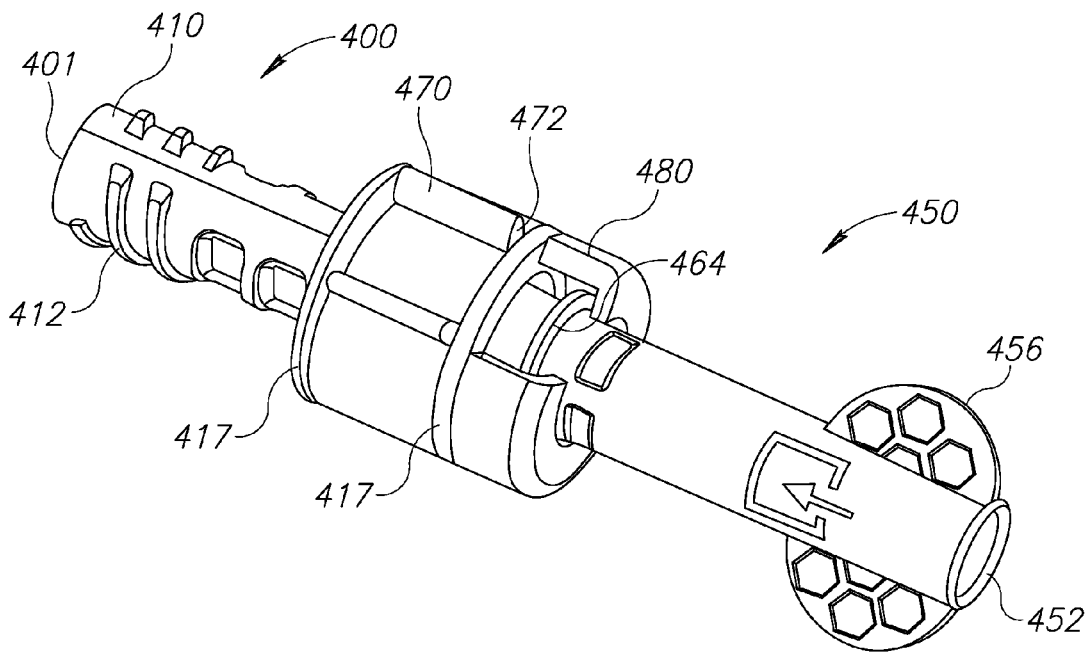

Reference is now made to FIG. 4A-FIG. 4B which show views of an adapter 400 before and after connection to a consumable end connector (CEC) 450, according to some embodiments. CEC 450 complies with the new ISO 80369 standard and is generally an integral part of a capnograph sampling line and patient interface (not shown). CEC 450 includes, at a distal end 451 thereof, threads 454, used for firm connection to a mating connector of the same standard. At its proximal end 452, CEC 450 includes wings 456, used for providing a firm grip to the user and ability to twist easily for mating purposes.

Adapter 400 includes a first end (A2D) 401 with a first connector 410 having a first connector configuration, here a connector configuration according to the ISO 594 standard, enabling adapter 400 to be screwed into a DIC of the same standard (not shown) using threads 412. A second end (A2C) 402 of adapter 400 is configured to receive CEC 450. According to this embodiment, adapter 400 further includes a locker, separate from adapter 400, such as snap-on locker 470, configured to be snapped around an indented wall 416 of the adapter, between limiting annular rings 417. Locker 470 may include a slot 472 configured to receive therewithin annular ring 417 closest to A2C 402. Attachment (and detachment) of CEC 450 may be performed without snap-on locker 470, by twisting and/or screwing threads 454 of CEC 450 into mating thread mechanism 420 of adapter 400. Alternatively, CEC may be screwed into adapter 400 while snap-on locker 470 is snapped therearound, such that screwing in CEC 450 lifts the ends of snap-on locker 470, facilitating threads 454 of CEC 450 to pass and lock. According to some embodiments, snap-on locker 470 may be welded to the adapter 400 after CEC 450 is secured to adapter 400.

After CEC 450 has been screwed into adapter 400 and snap-on locker 470 is snapped around adapter 400, CEC 450 is prevented from being unscrewed from adapter 400. Snap-on locker 470, includes an extension 480 configured to engage with a protruding section 464 on CEC 450. Extension 480 includes a rail 473 configured to receive protruding section 464 of CEC 450. According to some embodiments, rail 473 may be built of two (or more) spaced out limiting sections, and protruding section 464 may likewise be made of two (or more) sections, compatible with the number of sections in rail 473. Such configuration produces a lock and key formation preventing ISO 80369 connectors devoid protruding section(s) from connecting to adapter 400.

Upon connection of CEC 450 into adapter 400 and lockage of the assembly by snapping on snap-on locker 470, as depicted in FIG. 4B, the assembly serves as a single unit that may be screwed in and out of a device socket without being disassembled.

The assembly (CEC 450 connected to adapter 400) has an inherent ability to become either one of the connector configurations, by performing a minimal and simple manual action (not requiring an expert or technician). The hospital (or other end user) will therefore not be required to stock two types of consumables, i.e. one ending with an ISO 594 configuration connector and one with the new ISO 80369 configuration connector. Preferably, the consumable may, during the first few years of the transfer period, be marketed and distributed where it is ready for connection with an ISO 594 socket (the majority of devices in the field), and where to use it with the new ISO 80369 compatible device, the minimal manual action is required. That is, the double configuration connector is ready to connect to a DIC having an old connecter configuration through first connector 410 of adapter 400. However, if new devices having sockets compatible with the ISO 80369 standard are used, snap-on locker 470 may be removed, thereby enabling CEC 450 to be unscrewed from adapter 400. Since CEC 450 is in compatible with the ISO 80369 standard it will fit the ISO 80369 socket of the device.

According to some embodiments, snap-on locker 470 may be construed such that when removing it from adapter 400 it breaks. For example, snap-on locker 470 may include a breakage line, such as breakage line (not shown) made of a thinner wall thickness. It is understood to one of ordinary skill in the art that breakage of snap-on locker 470 renders it useless after removal.

When devices with the new ISO 80369 configuration socket become abundant, marketing of consumables that are compatible with the new standard device sockets can be initiated. Preferably, the consumables will be provided with an ISO 80369 connector devoid of protruding section(s).

Figure 5A:
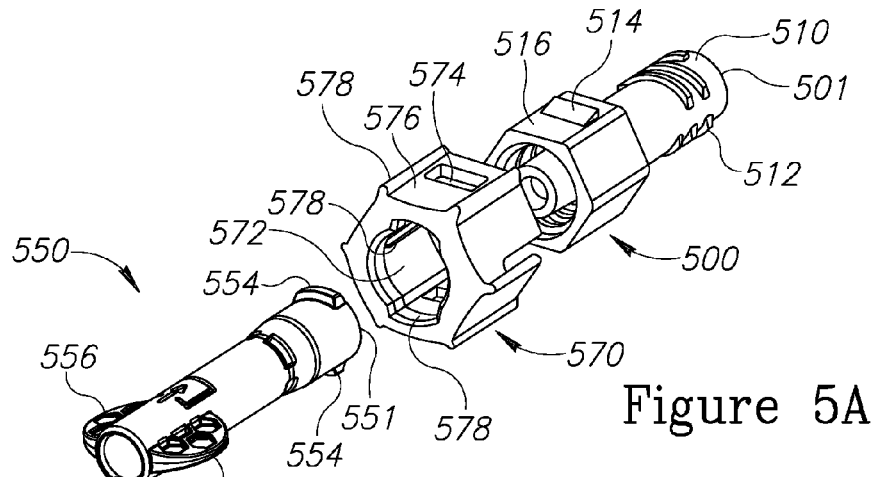
FIG. 5A and FIG. 5B show perspective views of an adapter before and after connection to a CEC, according to some embodiments.
Figures 5B, 5C:
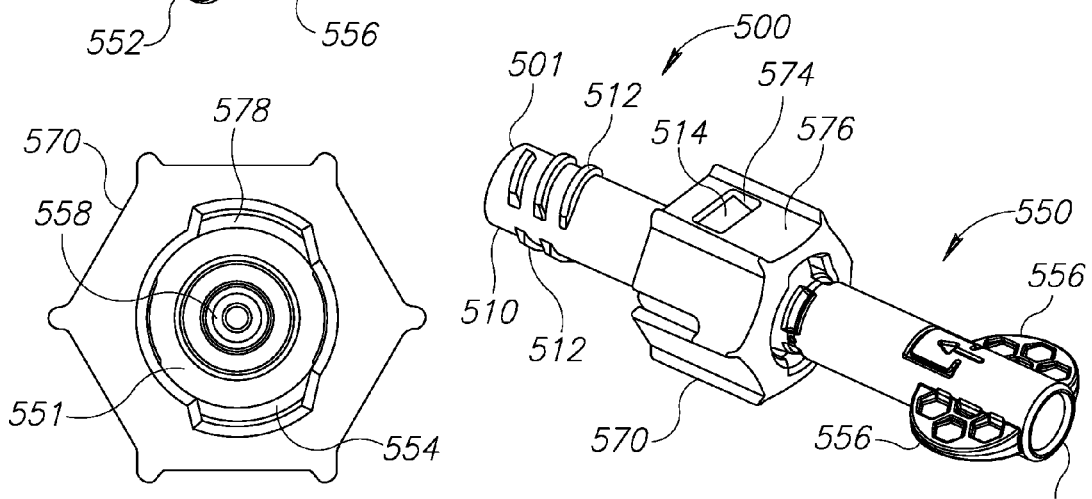
FIG. 5C shows a front view of an adapter, according to some embodiments.

Reference is now made to FIG. 5A-FIG. 5C, which show views of an adapter 500 before and after connection to a consumable end connector (CEC) 550, according to some embodiments. CEC 550 complies with the new ISO 80369 standard and is generally an integral part of a capnograph sampling line and patient interface (not shown). CEC 550 includes, at a distal end 551 thereof, threads 554, used for firm connection to a mating connector of the same standard. According to this embodiment, threads 554 are positioned asymmetrically on CEC 554. At its proximal end 552, CEC 550 includes wings 556, used for providing a firm grip to the user and ability to twist easily for mating purposes.

Adapter 500 includes a first end (A2D) 501 with a first connector 510 having a first connector configuration, here a connector configuration according to the ISO 594 standard, enabling adapter 500 to be screwed into a DIC 580 using threads 512. A second end (A2C) 502 of adapter 500 is configured to receive CEC 550. According to this embodiment, adapter 500 further includes a locker, separate from adapter 500, such as locker 570, configured to be pushed or slided over adapter 500. Locker 570 includes asymmetrical indentations 578 in an inner wall 572 thereof, configured to receive asymmetrical threads 554 of CEC 550 (see FIG. 3C). Attachment of CEC 550 to adapter 500 is performed by passing CEC 550 through locker 570, such that asymmetrical threads 554 slide through asymmetrical indentations 578, prior to screwing threads 554 of CEC 550 into mating thread mechanism 520 of adapter 500 or prior to pushing CEC 550 axially into adapter 500 as essentially described herein.

Adapter 500 also includes a protrusion 514 on an outer wall 516 thereof. Protrusion 514 is sized and shaped to be received within an opening 574 in an outer wall 576 of locker 570, thereby locking CEC 550 to adapter 500. According to some embodiments, locker 570 may be welded to the adapter 500 after CEC 550 is secured to adapter 500.

Upon connection of CEC 550 into adapter 500 and lockage of the assembly by sliding thereon locker 570, as depicted in FIG. 5B and FIG. 5C, the assembly serves as a single unit that may be screwed in and out a device socket without being disassembled.

The assembly (CEC 550 connected to adapter 500) has an inherent ability to become either one of the connector configurations, by performing a minimal and simple manual action (not requiring an expert or technician). The hospital (or other end user) will therefore not be required to stock two types of consumables, i.e. one ending with an ISO 594 configuration connector and one with the new ISO 80369 configuration connector. Preferably, the consumable may, during the first few years of the transfer period, be marketed and distributed where it is ready for connection with an ISO 594 socket (the majority of devices in field), and where to use it with the new ISO 80369 compatible device, the minimal manual action is required. That is, the double configuration connector is ready to connect to DIC 580 through first connector 510 of adapter 500. However, if new devices having sockets compatible with the ISO 80369 standard are used, locker 570 may be removed, thereby enabling CEC 550 to be screwed or pushed out of adapter 500. Since CEC 550 is in compatible with the ISO 80369 standard it will fit the ISO 80369 socket of the device. According to some embodiments, locker 570 may be construed such that when removing it from adapter 500 it breaks. It is understood to one of ordinary skill in art that breakage of locker 570 renders it useless after removal.

When devices with the new ISO 80369 configuration socket become abundant, marketing of consumables that are compatible with the new standard device sockets can be initiated. Such consumables will be provided with an ISO 80369 connector having symmetrically positioned threads incompatible with locker 570 and/or thread mechanism 520.

Figure 5D:
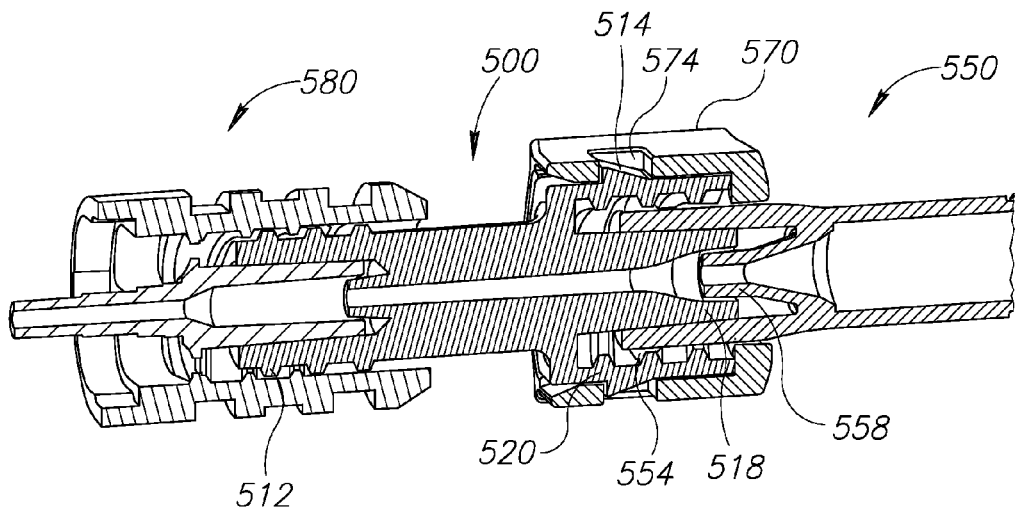
FIG. 5D shows a cross section of an adapter connected to a CEC and a DIC, according to some embodiments.

FIG. 5.D shows a cross section of adapter 500 connected to CEC 550 and to DIC 580, according to some embodiments. CEC is screwed into adapter 500 and subsequently locked thereto by securing protrusion 514 within opening 574, thereby preventing CEC 550 from being unscrewed from adapter 500. Furthermore, adapter 500 includes a secondary cone 518 configured to mate with a secondary cone 558 of CEC 550, thereby ensuring an air tight passageway with minimal disturbances to flow, from CEC 550 to adapter 500 and further to DIC 580, once securely assembled.

Figure 6A:
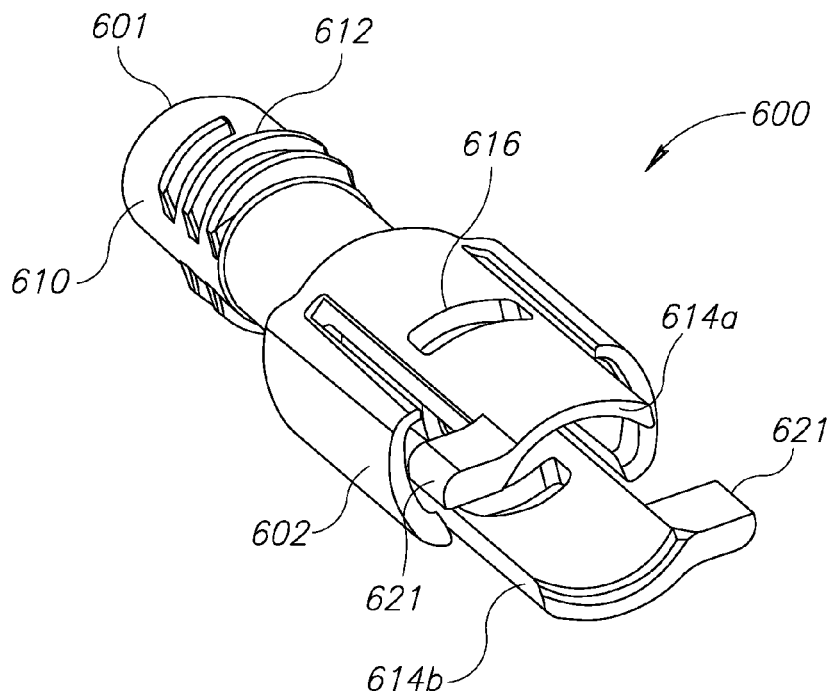
FIG. 6A shows a perspective view of an adapter, according to some embodiments.
Figure 6B:
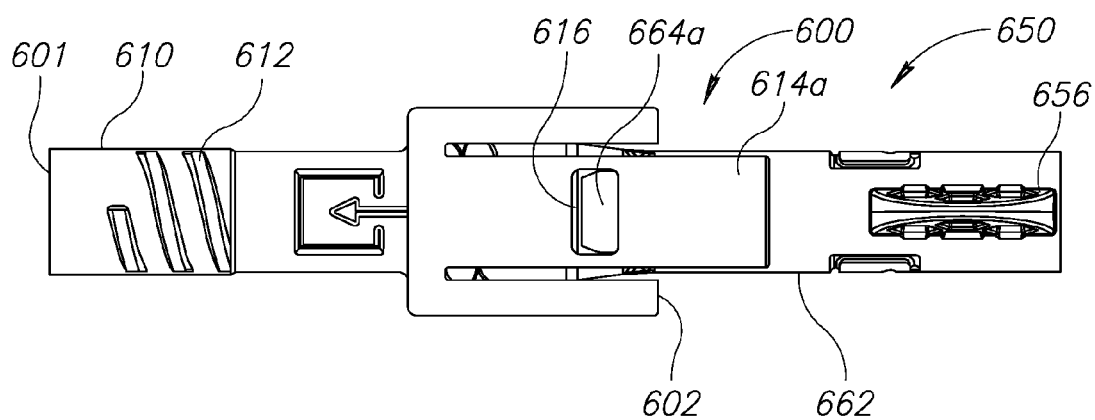
FIG. 6B and FIG. 6C show bird and side perspective views, respectively, of an adapter connected to a CEC, according to some embodiments.
Figure 6C:
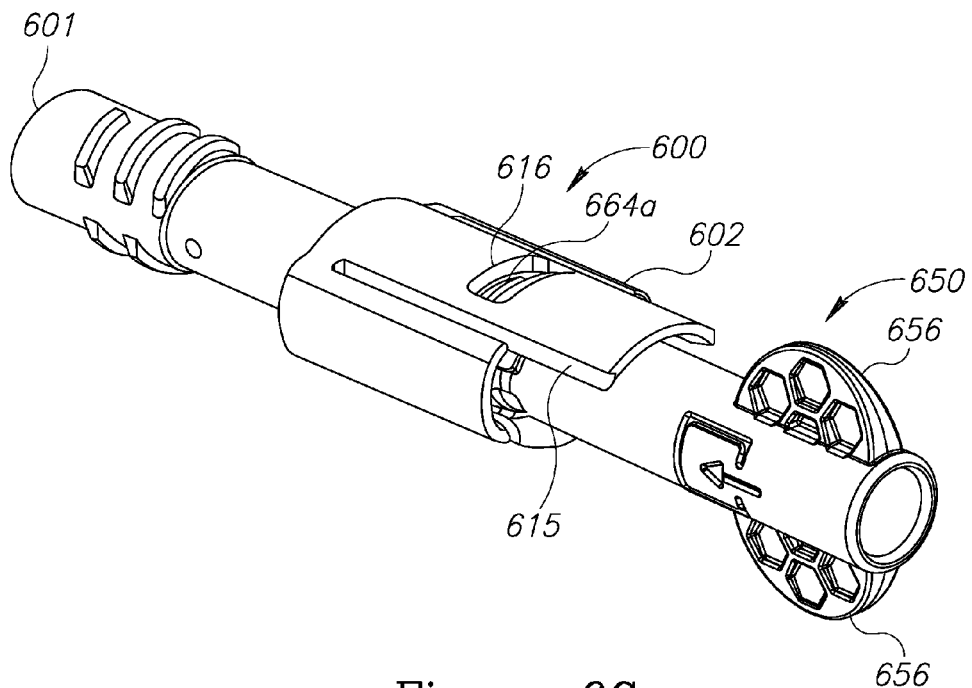

Reference is now made to FIG. 6A-FIG. 6C, which show views of an adapter 600 before and after connection to a consumable end connector (CEC) 650, according to some embodiments. CEC 650 complies with the new ISO 80369 standard and is generally an integral part of a capnograph sampling line and patient interface (not shown).

Adapter 600 includes a first end (A2D) 601 with a first connector 610 having a first connector configuration, here a connector configuration according to the ISO 594 standard, enabling adapter 600 to be screwed into DIC 680 using threads 612. A second end (A2C) 602 of adapter 600 is configured to receive CEC 650. According to this embodiment, adapter 600 includes latches 614a and 614b (also referred to herein as tongues). Latches 614a and 614b include at least one opening, such as opening 616 configured to receive and secure bulges 664a and 664b (also referred to herein as latching elements) on outer wall 662 of CEC 650, thereby locking CEC 650 to adapter 600. CEC 650 is here illustrated as including two bulges, however a larger number of bulges, such as 3, 4, 5 or more bulges complemented by a mating number of openings on latches 614a and/or 614b (compatible with the positioned of the bulges) may also be envisaged and as such fall within the scope of the present disclosure.

For connection, at least one of latches 614a and 614b is displaced outwards, enabling CEC 650 to slide axially into A2C 602 without screwing or twisting, in such manner that bulges 664a and 664b are positioned in line with openings 616 facilitating bulges 664a and 664b to be lodged within openings 616 of latches 614a and 614b. Latches 614a and/or 614b are sufficiently flexible to be lifted so as to accommodate bulges 664a and 664b during entrance. Thus mating is achieved by the key and lock feature of bulges 664a and 664b with openings 616 rather than through mating of A2C 602 with CEC 650. Latch 614a or 614b may be longer, thereby providing an extension 615 (shown in FIG. 6C) enabling gripping when removing CEC 650 from adapter 600. Bulges 664a and 664b, and openings 616 compatible therewith, may be of different size and shape. For example, bulge 664a, configured to be received within opening 616 of latch 614a having extension 615, may be shaped with a sharp angle (e.g. 90 degrees), while bulge 664b may have a larger angle facilitating easier release, after latch 614a has been released from bulge 664b. Furthermore, latches 614a and/or 614b may include a gripping elements 621 (shown in FIG. 6A) used when lifting latches 614a and/or 614b during connection and/or removal of CEC 650 to adapter 600.

Figure 6D:
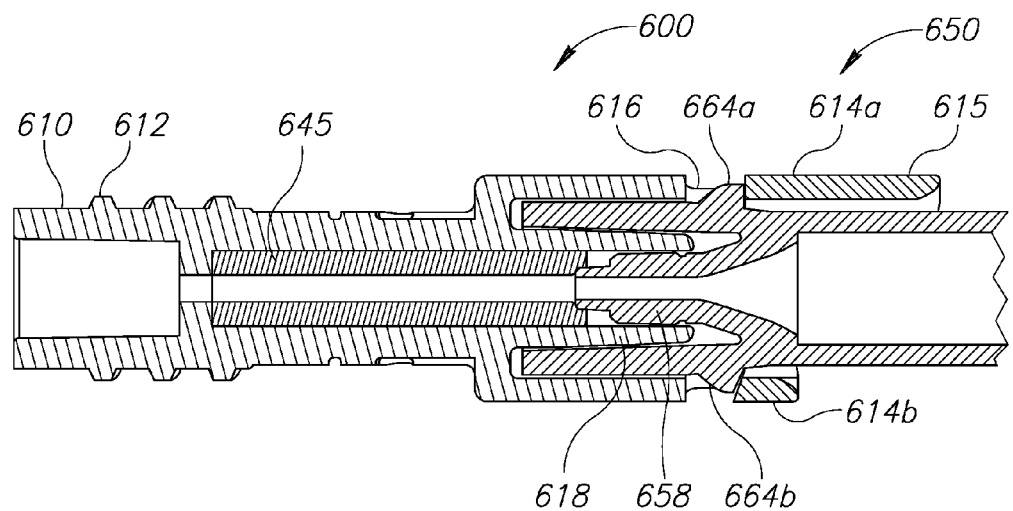
FIG. 6D shows a cross section of an adapter connected to a CEC, according to some embodiments.

Upon connection of CEC 650 into adapter 600, as depicted in FIGS. 6B and 6C, the assembly serves as a single unit that may be screwed in and out of DIC 680 without being disassembled, due to the latch and lock provided by latches 614a and 614b and bulges 664a and 664b (the latter shown in FIG. 6D).

The double configuration assembly (CEC 650 inserted into adapter 600) has an inherent ability to become either one of the connector configurations, by performing a minimal and simple manual action (not requiring an expert or technician). The hospital (or other end user) will therefore not be required to stock two types of consumables, i.e. one ending with an ISO 594 configuration connector and one with the new ISO 80369 configuration connector. It is preferable that the consumable, during the first few years of the transfer period, be marketed and distributed where it is ready for connection with the installed base, ISO 594 socket (the majority of devices in field), and where to use it with a new ISO 80369 compatible device, the minimal manual action is required. That is, the double configuration connector is ready to connect to a device socket having an old connecter configuration through first connector 610 of adapter 600. However, if devices having sockets compatible with the ISO 80369 standard are used, latch 614a may be lifted, (by gripping gripping elements 621), thereby enabling CEC 650 to be removed from adapter 600, by gripping wings 656 and twisting CEC 650 so as to release, initially bulge 664*a* from latch 614*a* and subsequently bulge 664*b* from latch 614*b*, thereby enabling CEC 650 to be pulled out of A2C 602. Since CEC 650 is compatible with the ISO 80369 standard, it will fit the ISO 80369 device socket.

After removal of CEC 650 from adapter 600, adapter 600 will not be usable again with any new standard ISO 80369 configuration connector that is not of the type that comes with the adapter (which anyway comes with an adapter). This is achieved since mating between CEC 650 and adapter 600 is only achieved by locking bulges 664*a* and 664*b* within opening 616 of latches 614*a* and 614*b* and not through mating between CEC 650 with A2C 602. Connectors devoid of bulges 664*a* and 664*b*, on the other hand, are not compatible with adapter 600. Therefore, saving adapter 600 will not add any benefit for further use, and will not serve as a means for future mating between DIC 680 and a new ISO 80369 connector, hence rendering adapter 600 useless after its first use. It is understood to one of ordinary skill in the art that such single use limitation is important in order to prevent buildup of a collection of adapters that negate the reason for creating the new standard, i.e. to reduce risk.

When devices with the new ISO 80369 configuration socket become abundant, marketing of consumables that are compatible with the new standard device sockets can be initiated. However, in order to ensure that these single configuration consumables do not connect with adapter 600, the consumables may be provided devoid of bulges 664*a* and 664*b*, thereby preventing them from connecting to adapter 600.

FIG. 6D, shows a cross section of adapter 600 connected to CEC 650 and to DIC 680, according to some embodiments. CEC 650 is connected to adapter 600 (without being inserted therein) to a point allowing bulges 664*a* and 664*b* to be hooked to be received within openings 616 of latches 614*a* and 614*b*, thereby preventing of CEC 650 from being pulled out of adapter 600. Adapter 600 includes a secondary cone 618 configured to mate with a secondary cone 658 of CEC 650, thereby ensuring an air tight passageway with minimal disturbances to flow from CEC 650 to adapter 600 and further to DIC 680, once securely assembled. According to some embodiments, adapter 600 may further include a soft material 645 configured to further ensure that the passageway from CEC 650 to adapter 600 and further to DIC 680 is kept airtight.

Figure 7A:
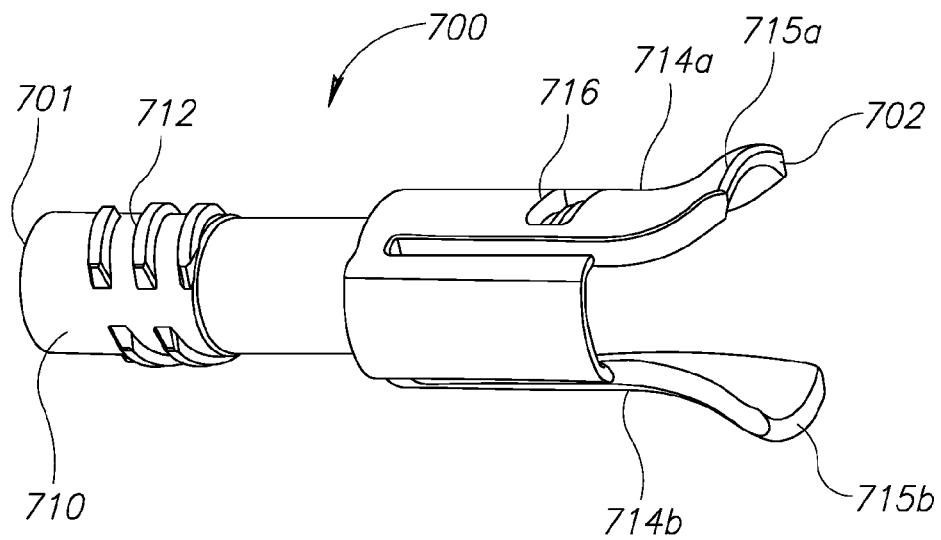
FIG. 7A shows a perspective view of an adapter, according to some embodiments.
Figure 7B:
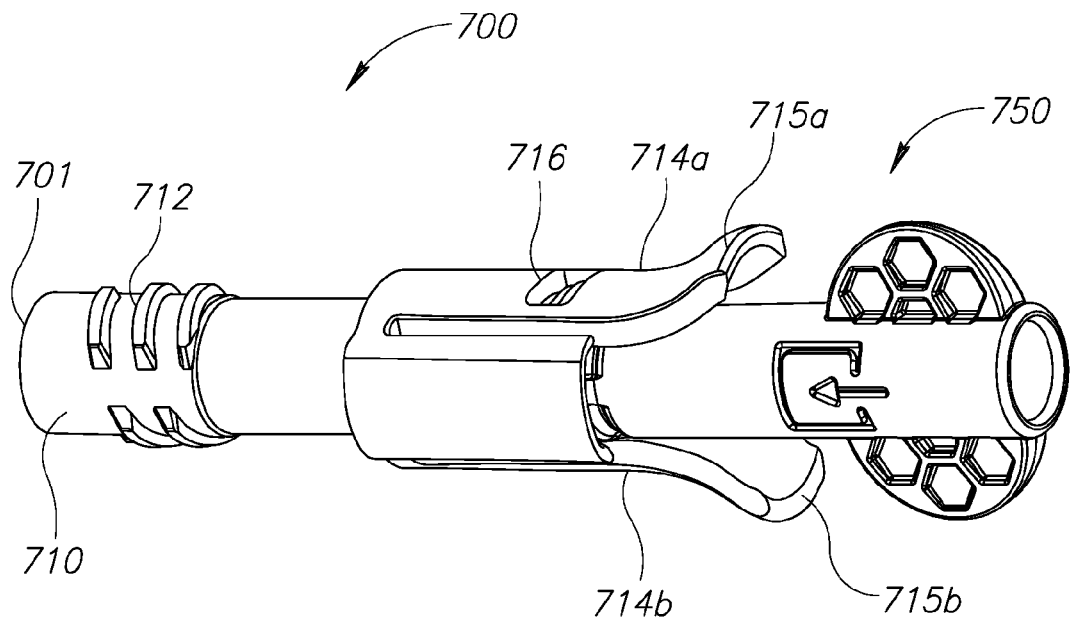
FIG. 7B shows a perspective view, of an adapter connected to a CEC, according to some embodiments.

Reference is now made to FIG. 7A and FIG. 7B which show views of an adapter 700, similar to the above embodiment, before and after connection to a consumable end connector (CEC) 750. CEC 750 complies with the new ISO 80369 standard and is generally an integral part of a capnograph sampling line and patient interface (not shown).

Adapter 700 includes a first end (A2D) 701 with a first connector 710 having a first connector configuration, here a connector configuration according to the ISO 594 standard, enabling adapter 700 to be screwed into DIC of the same standard using threads 712. A second end (A2C) 702 of adapter 700 is configured to receive CEC 750. According to this embodiment, adapter 700 includes latches 714*a* and 714*b* (also referred to herein as tongues). Latches 714*a* and 714*b* include at least one opening, such as opening 716 configured to receive and secure bulges (also referred to herein as latching elements and essentially similar to bulges 664*a* and 664*b* of CEC 650) formed on the outer wall of CEC 750, thereby locking CEC 750 to adapter 700.

For connection, at least one of latches 714*a* and 714*b* is displaced outwards enabling CEC 750 to slide axially into A2C 702 without screwing or twisting, in such manner that bulges of CEC 750 are positioned in line with openings 716 facilitating them to be lodged therewithin. Latches 714*a* and/or 714*b* are sufficiently flexible to be lifted and include curved extensions 715*a* and 715*b* facilitating easy gripping by a user.

Upon connection of CEC 750 into adapter 700, as depicted in FIG. 7B, the assembly serves as a single unit that may be screwed in and out of a DIC mateable with connector 710 of adapter 700, without being disassembled, due to the latch and lock provided by latches 714*a* and 714*b* and the bulges of CEC 750.

The double configuration assembly (CEC 750 inserted into adapter 700) has an inherent ability to become either one of the connector configurations, by performing a minimal and simple manual action (not requiring an expert or technician). The hospital (or other end user) will therefore not be required to stock two types of consumables, i.e. one ending with an ISO 594 configuration connector and one with the new ISO 80369 configuration connector. It is preferable, that the consumable, during the first few years of the transfer period, be marketed and distributed where it is ready for connection with the installed base, ISO 594 socket (the majority of devices in field), and where, to use it with a new ISO 80369 compatible device, the minimal manual action is required. That is, the double configuration connector is ready to connect to a device socket having an old connecter configuration through first connector 710 of adapter 700. However, if devices having sockets compatible with the ISO 80369 standard are used, latch 714*a* may be lifted by gripping curved extensions 715*a* and 715*b* and twisting CEC 750 so as to release the bulges from openings 716, enabling CEC 750 to be pulled out of A2C 702. Since CEC 750 is compatible with the ISO 80369 standard, it will fit the ISO 80369 device socket.

After removal of CEC 750 from adapter 700, adapter 700 will not be usable again with any new standard ISO 80369 configuration connector that is not of the type that comes with the adapter (which anyway comes with an adapter). This is achieved since mating between CEC 750 and adapter 700 is only achieved by locking the bulges within openings 716 of latches 714*a* and 714*b*, and not through mating between CEC 750 with A2C 702. Consequently, connectors devoid of bulges are not compatible with adapter 700. Therefore, saving adapter 700 will not add any benefit for further use, and will not serve as a means for future mating between DICs according to the ISO 594 standard and ISO 80369 connectors, hence rendering adapter 700 useless after its first use. It is understood to one of ordinary skill in the art that such single use limitation is important in order to prevent buildup of a collection of adapters that negate the reason for creating the new standard, i.e. to reduce risk.

When devices with the new ISO 80369 configuration socket become abundant, marketing of consumables that are compatible with the new standard device sockets can be initiated. However, in order to ensure that these single configuration consumables do not connect with adapter 700, the consumables may be provided devoid of bulges, thereby preventing them from connecting to adapter 700.

Figure 8:
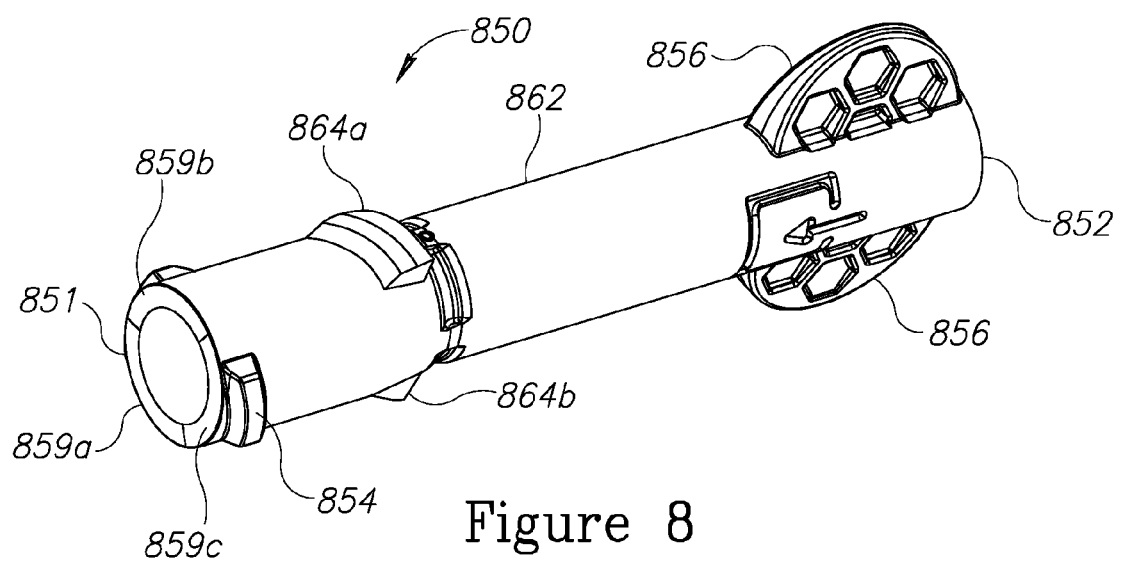
FIG. 8 shows a perspective view of CECs, according to some embodiments.

Reference is now made to FIG. 8, which shows a perspective view of a consumable end connector (CEC) 850, according to some embodiments. CEC 850 complies with the new ISO 80369 standard and is generally an integral part of a capnograph sampling line and patient interface (not shown). CEC 850 includes, at a distal end 851 thereof, threads 854, used for firm connection to a mating connector of the same standard. At a proximal end 852 thereof, CEC 850 includes wings 856, used for providing a firm grip to the user and ability to twist easily for mating purposes.

According to this embodiment, CEC 850 includes bulges 864a and 864b (also referred to herein as latching elements) on outer wall 862 of CEC 850. Bulges 864a and 864b are configured to be received within opening (such as opening 616) of latches formed on a compatible adapter (such as adapter 600), thereby providing a key and lock solution ensuring unique and firm connection between CEC 850 and the adapter. CEC 850 is here illustrated as including two bulges, however a larger number of bulges, such as 3, 4, 5 or more bulges may also be envisaged and as such fall within the scope of the present disclosure. According to some embodiments, CEC 850 may further include means to ensure activation of the medical device (e.g. capnograph) only when CEC 850 is connected to a (ISO 80369 standard) socket of the medical device or when an adapter, to which CEC 850 is connected, connects to a (ISO 594) socket of the medical device. Here, CEC 850 includes three spectrally distinct reflective regions 859a, 859b and 859c, each region configured to reflect light at a different wavelength when illuminated, configured to ensure activation of the medical device to which it is connected only when reflected light is identified, directly or indirectly.

Figure 9:
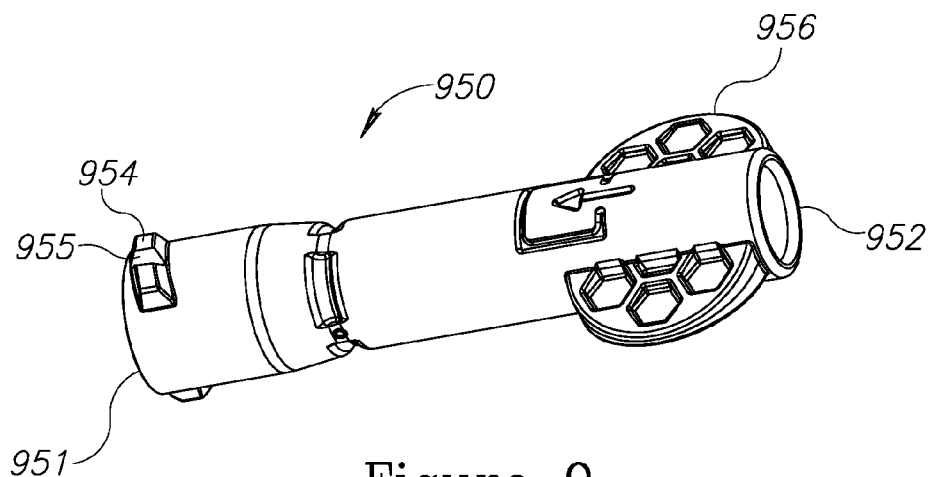
FIG. 9 shows a perspective view of CECs, according to some embodiments.

Reference is now made to FIG. 9, which shows a perspective view of a consumable end connector (CEC) 950, according to some embodiments. CEC 950 complies with the new ISO 80369 standard and is generally an integral part of a capnograph sampling line and patient interface (not shown). CEC 950 includes, at a distal end 951 thereof, threads 954, used for firm connection to a mating connector of the same standard. At a proximal end 952 thereof, CEC 950 includes wings 956, used for providing a firm grip to the user and ability to twist easily for mating purposes.

According to this embodiment, CEC 950 includes a notch 955 within thread 954. Notch 955 serve to provide a key and lock feature with a protrusion (such as protrusion 260) formed on an inner wall of an adapter ensuring unique connection between CEC 950 and the adapter. According to some embodiments, CEC 950 may further include means to ensure activation of the medical device (e.g. capnograph) only when CEC 950 is connected to a (ISO 80369 standard) socket of the medical device or when an adapter, to which CEC 950 is connected, connects to a (ISO 594) socket of the medical device, as essentially described herein.

Figure 10:
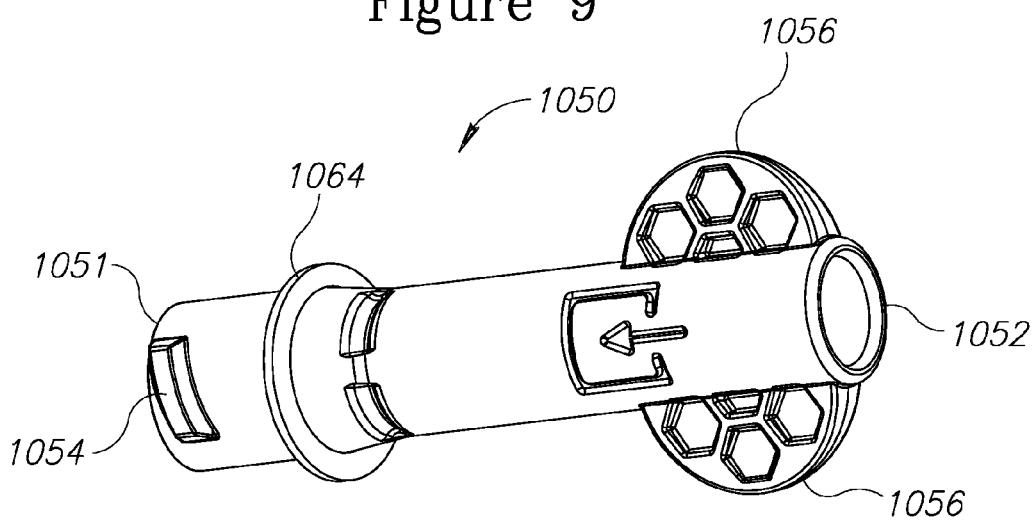
FIG. 10 shows a perspective view of CECs, according to some embodiments.

Reference is now made to FIG. 10, which shows a perspective view of a consumable end connector (CEC) 1050, according to some embodiments. CEC 1050 complies with the new ISO 80369 standard and is generally an integral part of a capnograph sampling line and patient interface (not shown). CEC 1050 includes, at a distal end 1051 thereof, threads 1054, used for firm connection to a mating connector of the same standard. At a proximal end 1052 thereof, CEC 1050 includes wings 1056, used for providing a firm grip to the user and ability to twist easily for mating purposes.

According to this embodiment, CEC 1050 includes a protruding section 1064, which serve to provide a key and lock feature with a rail (such as rail 480) ensuring a unique connection between CEC 1050 and the adapter. According to some embodiments, CEC 1050 may further include means to ensure activation of the medical device (e.g. capnograph) only when CEC 1050 is connected to a (ISO 80369 standard) socket of the medical device or when an adapter, to which CEC 1050 is connected, connects to a (ISO 594) socket the medical device, as essentially described herein.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. An adapter for use in a respiratory gas sampling and/or delivery tubing systems, the adapter configured to allow interconnection of a device input connector (DIC) having a first connector configuration and a tube end connector (CEC) having a second connector configuration, the adapter comprising:
   a first end comprising a first connector mateable with the DIC;
   a second end configured to receive at least part of the CEC;
   a locking/release mechanism configured to lock/release the CEC to/from the adapter wherein the locking/release mechanism comprises at least one latch configured to hook onto the CEC; and
   a secondary cone disposed on the second end and forming at least a portion of a distal-most terminus of the adapter, wherein the secondary cone comprises a central bore extending from the distal-most terminus toward the first end along a longitudinal axis of the adapter, and wherein a diameter of the central bore decreases along the longitudinal axis from the second end to the first end.

2. The adapter of claim 1, wherein the locking/release mechanism is configured to prevent connection and/or disconnection of the first connector to and/or from the DIC from releasing the CEC from the adaptor.

3. The adapter of claim 1, wherein the secondary cone is formed within a void of the adapter such that the secondary cone is spaced apart and at least partially surrounded by the locking/release mechanism, and the secondary cone is configured to mate with a secondary cone formed within a void of the CEC, thereby forming an airtight passageway throughout the adapter and the CEC.

4. The adapter of claim 1, being non-reusable after activation of the locking/release mechanism.

5. The adapter of claim 1, comprising at least one feature rendering it incompatible with a new CEC after a first use.

6. The adapter of claim 1, wherein the latch is configured to hook onto a thread located on an outer wall of the CEC.

7. The adapter of claim 6, wherein the latch comprises a protrusion in an inner wall thereof, the protrusion configured to be received within a notch formed within the thread.

8. The adapter of claim 6, wherein lifting the latch by the thread when the CEC is twisted in a counter-clockwise direction relative to the adapter releases the CEC from the adapter.

9. The adapter of claim 6, wherein the latch comprises an opening configured to receive a bulge located on an outer wall of the CEC; wherein lifting the latch frees the bulge from the opening, thereby enabling release of the CEC from said adapter.

10. The adapter of claim 1, further comprising a feature visibly distinguishing the adapter from the CEC.

11. The adapter of claim 1, further comprising a tube interconnecting between the first end and the second end of the adapter.

* * * * *